(12) United States Patent
Pinney et al.

(10) Patent No.: US 7,091,240 B2
(45) Date of Patent: Aug. 15, 2006

(54) TUBULIN BINDING LIGANDS AND CORRESPONDING PRODRUG CONSTRUCTS

(75) Inventors: Kevin G. Pinney, Woodway, TX (US); Vani P. Mocharla, Waco, TX (US); Zhi Chen, Hamden, CT (US); Charles M. Garner, Waco, TX (US); Mallinath Hadimani, Waco, TX (US); Raymond Kessler, Sugarland, TX (US); James M. Dorsey, Durham, NC (US); Klaus Edvardsen, Klampenborg (DK); David J. Chaplin, Watlington (CA); Joseph Prezioso, Boston, MA (US); Anjan Ghatak, deceased, late of Salt Lake City, UT (US); by Usha Ghatak, legal representative, Salt Lake City, UT (US)

(73) Assignees: Oxigene, Inc., Watertown, MA (US); Baylor University, Waco, TX (US)

( * ) Notice: Subject to any disclaimer, the term of this patent is extended or adjusted under 35 U.S.C. 154(b) by 26 days.

(21) Appl. No.: 10/425,462

(22) Filed: Apr. 29, 2003

(65) Prior Publication Data

US 2004/0044059 A1 Mar. 4, 2004

Related U.S. Application Data

(63) Continuation-in-part of application No. 09/804,280, filed on Mar. 12, 2001, now Pat. No. 6,593,374.

(60) Provisional application No. 60/188,295, filed on Mar. 10, 2000.

(51) Int. Cl.
*A61K 31/34* (2006.01)
*C07D 307/93* (2006.01)

(52) U.S. Cl. .................... 514/469; 549/468
(58) Field of Classification Search ........... 549/468; 514/469
See application file for complete search history.

(56) References Cited

U.S. PATENT DOCUMENTS

| 3,448,190 A | * | 6/1969 | Baron et al. ............ 424/59 |
|---|---|---|---|
| 4,133,814 A | | 1/1979 | Jones et al. ........ 260/326.55 A |
| 4,656,187 A | | 4/1987 | Black et al. ................ 514/422 |
| 5,532,382 A | | 7/1996 | Carlson et al. .............. 549/57 |
| 5,596,106 A | * | 1/1997 | Cullinan et al. ............. 549/57 |
| 5,886,025 A | | 3/1999 | Pinney ....................... 514/443 |
| 5,952,350 A | | 9/1999 | Cullinan et al. ............ 514/319 |
| 5,958,916 A | | 9/1999 | Bryant et al. ............... 514/212 |
| 6,162,930 A | | 12/2000 | Pinney et al. ................ 549/57 |
| 6,166,069 A | * | 12/2000 | Malamas et al. .......... 514/469 |
| 6,350,777 B1 | | 2/2002 | Pinney et al. .............. 514/469 |

FOREIGN PATENT DOCUMENTS

| EP | 1 028 110 A1 | 8/2000 |
|---|---|---|
| WO | WO 96/40137 | 12/1996 |
| WO | WO 98/39323 | 9/1998 |
| WO | WO 01/68654 A2 | 9/2001 |
| WO | WO 01/77093 A1 | 10/2001 |
| WO | WO 01/79180 A2 | 10/2001 |
| WO | WO 02/060872 A1 | 8/2002 |

OTHER PUBLICATIONS

Bai et al. *Cancer Res.*, 56(19):4398-4406 (1996).
Boyd et al. *Drug Dev. Res.*, 34:91-109 (1995).
Chaplin et al. *Anticancer Res.*, 19:189-196 (1999).

* cited by examiner

*Primary Examiner*—Deborah C. Lambkin
(74) *Attorney, Agent, or Firm*—Ivor R. Elrifi; Naomi S. Biswas, Esq.; Mintz Levin

(57) ABSTRACT

A diverse set of tubulin binding agents have been discovered which are structurally characterized, in a general sense, by a semi-rigid molecular framework capable of maintaining aryl-aryl, pseudo pi stacking distances appropriate for molecular recognition of tubulin. In phenolic or amino form, these ligands may be further functionalized to prepare phosphate esters, phosphate salts, phosphoramidates, and other prodrugs capable of demonstrating selective targeting and destruction of tumor cell vasculature.

28 Claims, 9 Drawing Sheets

TUBULIN BINDING LIGANDS AND CORRESPONDING PRODRUG CONSTRUCTS

CROSS-REFERENCE TO RELATED APPLICATIONS

This is a Continuation-In-Part of U.S. patent application Ser. No. 09/804,280, filed Mar. 12, 2001, now U.S. Pat. No. 6,593,374 which itself claims priority to U.S. provisional patent application Ser. No. 60/188,295 filed on Mar. 10, 2000. This application also claims the priority benefit of copending U.S. patent application Ser. No. 10/218,833, filed Aug. 14, 2002, which itself claims priority to both U.S. patent application Ser. No. 09/505,402, filed Feb. 16, 2000 and U.S. provisional patent application Ser. No. 60/120,478, filed Feb. 18, 1999. Attention is called to U.S. Pat. No. 6,162,930 issued to Pinney et al. on Dec. 19, 2000, which is incorporated in its entirety by reference herein. The following citations are incorporated in pertinent part by reference herein for the reasons cited.

BACKGROUND OF THE INVENTION

The cytoskeletal protein tubulin is among the most attractive therapeutic drug targets for the treatment of solid tumors. A particularly successful class of chemotherapeutics mediates its anti-tumor effect through a direct binding interaction with tubulin. This clinically-promising class of therapeutics, called Tubulin Binding Agents, exhibit potent tumor cell cytotoxicity by efficiently inhibiting the polymerization of $\alpha\beta$-tubulin heterodimers into the microtubule structures that are required for facilitation of mitosis or cell division (Hamel, Medicinal Research Reviews, 1996).

Currently, the most recognized and clinically useful anti-tumor agents are Vinca Alkaloids, such as Vinblastine and Vincristine (Owellen et al, Cancer Res., 1976; Lavielle et al, J. Med. Chem., 1991) along with Taxanes such Taxol (Kingston, J. Nat. Prod., 1990; Schiff et al, Nature, 1979; Swindell et al, J. Cell Biol., 1981). Additionally, natural products such as Rhizoxin (Nakada et al, Tetrahedron Lett., 1993; Boger et al, J. Org. Chem., 1992; Rao, et al, Tetrahedron Lett., 1992; Kobayashi et al, Pure Appl. Chem., 1992; Kobayashi et al, Indian J. Chem., 1993; Rao et al, Tetrahedron Lett., 1993), the Combretastatins (Lin et al, Biochemistry, 1989; Pettit et al, J. Nat. Prod., 1987; Pettit et al, J. Org. Chem., 1985; Pettit et al, Can. J. Chem., 1982; Dorr et al, Invest. New Drugs, 1996), Curacin A (Gerwick et al, J. Org. Chem., 59:1243, 1994), Podophyllotoxin (Hammonds et al, J. Med. Microbiol, 1996; Coretese et al, J. Biol. Chem., 1977), Epothilones A and B (Nicolau et al., Nature, 1997), Dolastatin-10 (Pettit et al, J. Am. Chem. Soc., 1987; Pettit et al, Anti-Cancer Drug Des., 1998), and Welwistatin (Zhang et al, Molecular Pharmacology, 1996), as well as certain synthetic analogues including Phenstatin (Pettit G R et al., J. Med. Chem., 1998), 2-styrylquinazolin-4(3H)-ones ("SQOs", Jiang et al, J. Med. Chem., 1990), and highly oxygenated derivatives of cis- and trans-stilbene and dihydrostilbene (Cushman et al, J. Med. Chem., 1991) are all known to mediate their tumor cytotoxic activity through tubulin binding and subsequent inhibition of mitosis.

Normally, during the metaphase of cell mitosis, the nuclear membrane has broken down and tubulin is able to form centrosomes (also called microtubule organizing centers) which facilitate the formation of a microtubule spindle apparatus to which the dividing chromosomes become attached. Subsequent polymerization and depolymerization of the spindle apparatus mitigates the separation of the daughter chromosomes during anaphase such that each daughter cell contains a full complement of chromosomes. As antiproliferatives or antimitotic agents, Tubulin Binding Agents exploit the relatively rapid mitosis that occurs in proliferating tumor cells. By binding to tubulin and inhibiting the formation of the spindle apparatus in a tumor cell, the Tubulin Binding Agent can cause significant tumor cell cytotoxicity with relatively minor effects on the slowly-dividing normal cells of the patient.

The exact nature of tubulin binding site interactions remain largely unknown, and they definitely vary between each class of Tubulin Binding Agent. Photoaffinity labeling and other binding site elucidation techniques have identified three key binding sites on tubulin: 1) the Colchicine site (Floyd et al, Biochemistry, 1989; Staretz et al, J. Org. Chem., 1993; Williams et al, J. Biol. Chem., 1985; Wolff et al, Proc. Natl. Acad. Sci. U.S.A., 1991),2) the Vinca Alkaloid site (Safa et al, Biochemistry, 1987), and 3) a site on the polymerized microtubule to which taxol binds (Rao et al, J. Natl. Cancer Inst., 1992; Lin et al, Biochemistry, 1989; Sawada et al, Bioconjugate Chem, 1993; Sawada et al, Biochem. Biophys. Res. Commun., 1991; Sawada et al, Biochem. Pharmacol., 1993). An important aspect of this work requires a detailed understanding, at the molecular level, of the "small molecule" binding domain of both the $\alpha$ and $\beta$ subunits of tubulin. The tertiary structure of the $\alpha,\beta$ tubulin heterodimer was reported in 1998 by Downing and co-workers at a resolution of 3.7 Å using a technique known as electron crystallography (Nogales et al, Nature, 1998). This brilliant accomplishment culminates decades of work directed toward the elucidation of this structure and should facilitate the identification of small molecule binding sites, such as the colchicine site, using techniques such as photoaffinity and chemical affinity labeling (Chavan et al, Bioconjugate Chem., 1993; Hahn et al, Photochem. Photobiol., 1992).

An aggressive chemotherapeutic strategy for the treatment and maintenance of solid tumor cancers continues to rely on the development of architecturally new and biologically more potent Tubulin Binding Agents which mediate their effect through a direct binding interaction with tubulin. The present invention addresses this urgent need by providing a structurally novel class of Tubulin Binding Agent compositions with potent antiproliferative activity and tumor cell cytotoxicity. In addition, the present invention provides the important discovery that corresponding prodrug constructs of these agents have selective effects on the tumor vasculature which are independent of its primary antimitotic effects on the tumor itself. These agents are capable of selectively shutting down the flow of blood to a tumor and causing secondary tumor cell death. Thus the present compositions have expanded clinical utility over known tubulin binding agents.

SUMMARY OF THE INVENTION

The present invention relates to a discovery of Tubulin Binding Agents that result from the judicious combination of a non-tubulin binding molecular template which, when suitably modified with structural features such as phenolic moieties and arylalkoxy groups, is found to inhibit tubulin polymerization and tumor cell proliferation.

One important aspect of the present invention provides a compound of the following general formula I:

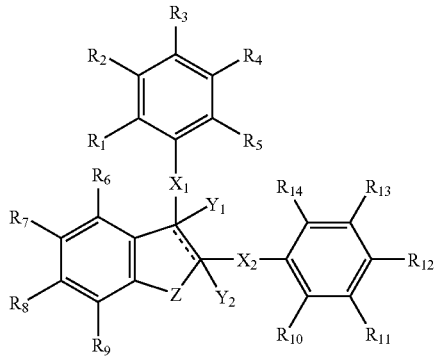

Formula I wherein:

$R_1$ through $R_{14}$ are independently selected from the group comprising H, OH, Alkyl, Aryl, Benzyl, Amine, Halogen, Lower Alkoxy, Phosphate, Phosphoramidate, or Amino Acid Acyl,

- - - - - is optionally a single or double covalent bond, $Y_1$ and $Y_2$ are optionally H or OH when - - - - - is a single covalent bond, $X_1$ and $X_2$ are optionally a single covalent bond, oxygen, or a carbonyl group, and Z is optionally $CH_2$, O, N, or S.

In a more specific embodiment, the present invention focuses on benzo[b]thiophene ("BbT") derivatives, particularly a compound of the following general Formula Ia:

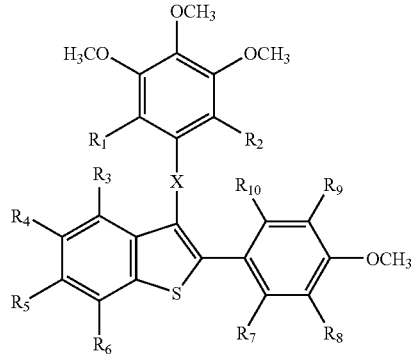

Formula Ia wherein:

$R_1$ through $R_{10}$ are independently selected from the group consisting of H, OH, Halogen, Amine, Alkyl, Aryl, Benzyl, Lower Alkoxy, Phosphate, Phosphoramidate, or Amino Acid Acyl; and X is a single covalent bond, an oxygen, or a carbonyl group.

In another embodiment, the present invention provides Benzo[b]Furan ("BbF") derivatives, particularly a compound of the following general Formula Ib:

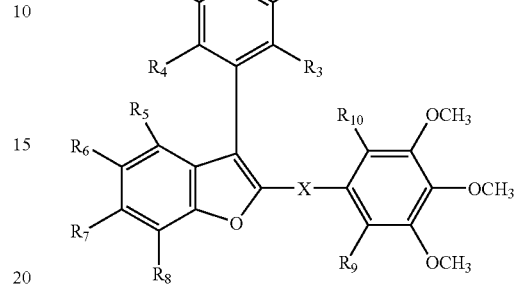

Formula Ib wherein:

$R_1$ through $R_{10}$ are independently selected from the group consisting of H, OH, Halogen, Amine, Alkyl, Aryl, Benzyl, Lower Alkoxy, Phosphate, Phosphoramidate, or Amino Acid Acyl; and X is a single covalent bond, an oxygen, or a carbonyl group.

A particularly preferred BbF derivative is the diphosphate prodrug compound of the following structure (1):

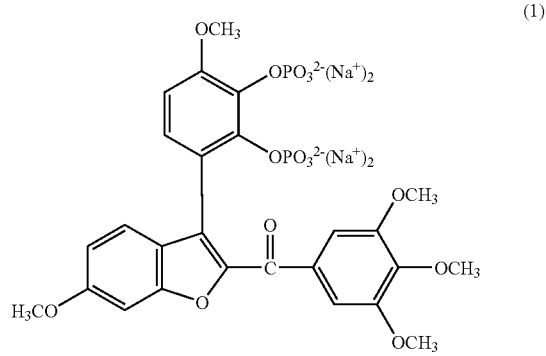

(1)

In a second aspect, the present invention provides Indene and Indane derivatives, particularly compounds of the following general Formula II:

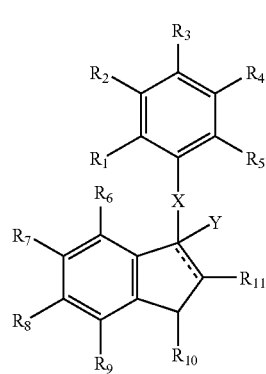

Formula II wherein:

$R_1$ through $R_{11}$ are optionally selected from the group consisting of H, OH, Alkyl, Aryl, Benzyl, Amine, Lower Alkoxy, Phosphate, Phosphoramidate, or Amino Acid Acyl Group;

----- is optionally a single or double covalent bond, with the proviso that Y is H or OH when ----- is a single covalent bond; and X is optionally a single covalent bond, oxygen, or carbonyl group.

In another separate aspect, the present invention provides Enediyne derivatives, particularly compounds of the following general Formula III:

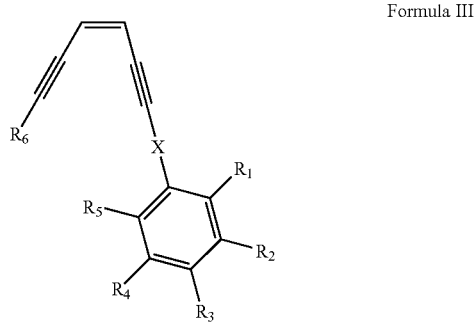

Formula III wherein:

$R_1$ through $R_6$ are optionally selected from the group H, OH, Alkyl, Aryl, Benzyl, Amine, Lower Alkoxy, Phosphate, Phosphoramidate, or Amino Acid Acyl Group, and X is optionally a single covalent bond, oxygen, or carbonyl group.

In a fourth aspect, the invention contemplates methods of contacting a tubulin-containing system with an effective amount of a compound of Formula I, II, or III. Methods are also provided for treating a warm-blooded animal afflicted with a neoplastic disease comprising administering an effective amount of compound capable of inhibiting the proliferation of the neoplastic disease. In a preferred embodiment, the antiproliferative effect has the direct result of causing tumor cell cytotoxicity due to inhibition of mitosis.

In a fifth aspect, the invention broadly contemplates the provision of a method for treating a warm-blooded animal having a vascular proliferative disorder comprising administering an effective amount of a compound of the present invention to achieve targeted vascular toxicity at a locality of proliferating vasculature, wherein in the proliferating vasculature is malignant or nonmalignant.

In yet another aspect, the invention broadly contemplates the provision of a method for administering an effective amount of a compound of the present invention to selectively reduce the flow of blood to at least a portion of a neoplastic region, thereby causing substantial necrosis of tissue in the neoplastic region without substantial necrosis of tissue in adjoining regions. In a preferred embodiment, the effect of reduced tumor blood flow is reversible so that normal tumor blood flow is restored following cessation of treatment.

The details of one or more embodiments of the invention are set forth in the accompanying description below. Although any methods and materials similar or equivalent to those described herein can be used in the practice or testing of the present invention, the preferred methods and materials are now described. Other features, objects, and advantages of the invention will be apparent from the description. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs.

DETAILED DESCRIPTION OF THE INVENTION

Figure 1:
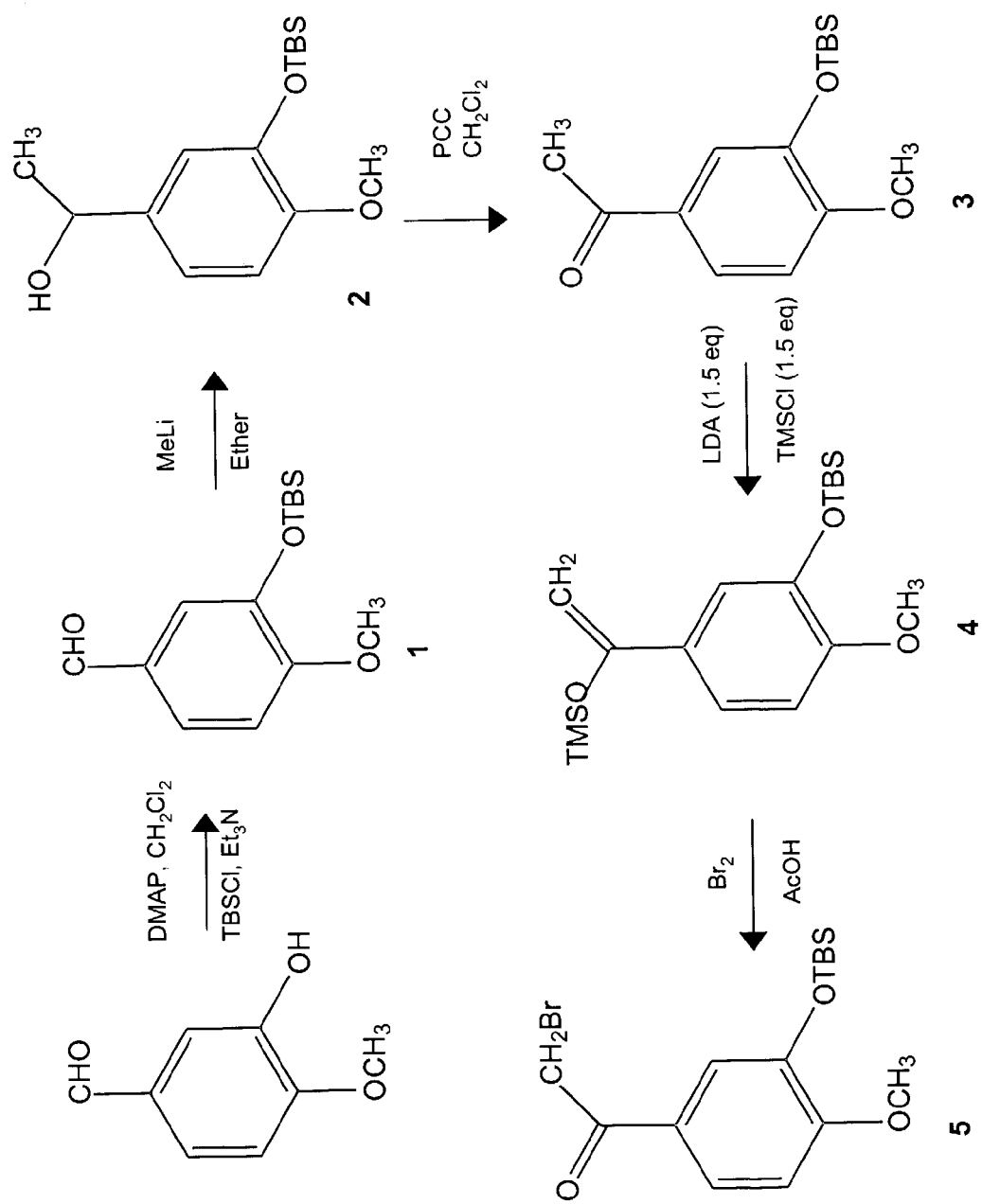
FIG. 1 illustrates a synthetic route for large-scale preparation of starting materials required for synthesis of tubulin binding agents.

The compounds of the present invention demonstrate remarkable cytotoxicity against a variety of human cancer cell lines. The ability of an agent to inhibit tubulin polymerization and microtubule formation is an important property of many anticancer agents. Disruption of microtubules that comprise the cytoskeleton and mitotic spindle apparatus can interfere dramatically with the ability of a cell to successfully complete cell division. The compounds of the present invention are highly cytotoxic to actively proliferating cells, inhibiting mitotic division and often causing selective apoptosis of tumor cells, while leaving normal quiescent cells relatively unaffected.

Further significance is given to new drugs that bind to the colchicine site since it has recently been shown that many tubulin binding agents which bind to this site also demonstrates activity on against malignant proliferating vasculature. Antivascular chemotherapy is an emerging area of cancer chemotherapy which centers on the development of drugs, called Vascular Targeting Agents ("VTAs") or vascular damaging agents, that selectively target the vasculature of tumor cells rather than the tumor cells themselves. Much of the research in anti-vascular cancer therapy has focused on understanding the process of new blood vessel formation, known as angiogenesis, and identifying anti-angiogenic agents which inhibit the formation of new blood vessels. Angiogenesis is characterized by the proliferation of tumor endothelial cells and generation of new vasculature to support the growth of a tumor. This growth is stimulated by certain growth factors produced by the tumor itself. One of these growth factors, Vascular Endothelial Growth Factor ("VEGF"), is relatively specific towards endothelial cells, by virtue of the restricted and up-regulated expression of its cognate receptor. Various anti-angiogenic strategies have been developed to inhibit this signaling process at one or more steps in the biochemical pathway in order to prevent the growth and establishment of the tumor vasculature. However, anti-angiogenic therapies act slowly and must be chronically administered over a period of months to years in order to generate their desired effect.

In contrast to Anti-angiogeneic agents, VTAs attack solid tumors by selectively targeting the established tumor vasculature and causing extensive shutdown of tumor blood flow. A single dose of VTA can cause a rapid and selective shutdown of the tumor neovasculature within a period of minutes to hours, leading eventually to tumor necrosis by induction of hypoxia and nutrient depletion. This vascular-mediated cytotoxic mechanism of VTA action is quite divorced from that of anti-angiogenic agents which inhibit the formation of new tumor vasculature rather than disrupting the existing tumor vasculature. Other agents have been known to disrupt tumor vasculature but differ in that they also manifest substantial normal tissue toxicity at their maximum tolerated dose. In contrast, genuine VTAs retain their vascular shutdown activity at a fraction of their maximum tolerated dose.

Combretastatin A-4 Disodium Phosphate Prodrug ("CA4DP") is the lead drug of a group of Tubulin-binding VTAs currently in clinical trials (U.S. Pat. No.5,561,122; Chaplin et al, Anticancer Res., 1999; Tozer et al, Cancer Res., 1999; Pettit and Rhodes, Anti-Cancer Drug Des., 1998; Iyer et al, Cancer Res., 1998; Dark et al, Cancer Res., 1997). Other Tubulin binding VTAs that have been discovered include the Colchicinoid ZD6126 (Davis et al., Cancer Research, 2002 ) and the Combretastatin analog AVE8032 (Lejeune et al, Proceedings of the AACR., 2002). It is thought that Tubulin-binding VTAs selectively destabilize the microtubule cytoskeleton of tumor endothelial cells, causing a profound alteration in the shape of the cell which ultimately leads to occlusion of the tumor blood vessel and shutdown of blood flow to the tumor (Galbraith et al., Anticancer Research, 2001; Kanthou et al, Blood, 2002). The inventors have discovered that the compounds of Formulas I II, and III as well as analogs thereof, can also function as VTAs, and thus are useful for the treatment of malignant vascular proliferative disorders, such as solid tumor cancers, as well as other nonmalignant vascular proliferative disorders, including retinal neovascularization and restenosis.

In one embodiment, the present invention is directed to the administration of a vascular targeting agent ("VTA"), particularly a tubulin binding agent, for the treatment of malignant or non-malignant vascular proliferative disorders in ocular tissue.

Neovascularization of ocular tissue is a pathogenic condition characterized by vascular proliferation and occurs in a variety of ocular diseases with varying degrees of vision failure. The administration of a VTA for the pharmacological control of the neovascularization associated with non-malignant vascular proliferative disorders such as wet macular degeneration, proliferative diabetic retinopathy or retinopathy of prematurity would potentially benefit patients for which few therapeutic options are available. In another embodiment, the invention provides the administration of a VTA for the pharmacological control of neovascularization associated with malignant vascular proliferative disorders such as ocular tumors.

The blood-retinal barrier (BRB) is composed of specialized nonfenestrated tightly-joined endothelial cells that form a transport barrier for certain substances between the retinal capillaries and the retinal tissue. The nascent vessels of the cornea and retina associated with the retinopathies are aberrant, much like the vessels associated with solid tumors. Tubulin binding agents, inhibitors of tubulin polymerization and vascular targeting agents may be able to attack the aberrant vessels because these vessels do not share architectural similarities with the blood retinal barrier. Tubulin binding agents may halt the progression of the disease much like they do with tumor-associated vasculature.

The compounds of the present invention may also be used in the treatment of vascular disease, particularly atherosclerosis and restenosis. Atherosclerosis is the most common form of vascular disease and leads to insufficient blood supply to critical body organs, resulting in heart attack, stroke, and kidney failure. Additionally, atherosclerosis causes major complications in those suffering from hypertension and diabetes, as well as tobacco smokers. Atherosclerosis is a form of chronic vascular injury in which some of the normal vascular smooth muscle cells ("VSMC") in the artery wall, which ordinarily control vascular tone regulating blood flow, change their nature and develop a "cancer-like" behavior. These VSMC become abnormally proliferative, secreting substances (growth factors, tissue-degradation enzymes and other proteins) which enable them to invade and spread into the inner vessel lining, blocking blood flow and making that vessel abnormally susceptible to being completely blocked by local blood clotting, resulting in the death of the tissue served by that artery.

Restenosis, the recurrence of stenosis or artery stricture after corrective surgery, is an accelerated form of atherosclerosis. Recent evidence has supported a unifying hypothesis of vascular injury in which coronary artery restenosis along with coronary vein graft and cardiac allograft atherosclerosis can be considered to represent a much accelerated form of the same pathogenic process that results in spontaneous atherosclerosis. Restenosis is due to a complex series of fibroproliferative responses to vascular injury involving potent growth-regulatory molecules, including platelet-derived growth factor (PDGF) and basic fibroblast growth factor (bFGF), also common to the later stages in atherosclerotic lesions, resulting in vascular smooth muscle cell proliferation, migration and neointimal accumulation.

Restenosis occurs after coronary artery bypass surgery (CAB), endarterectomy, and heart transplantation, and particularly after heart balloon angioplasty, atherectomy, laser ablation or endovascular stenting (in each of which one-third of patients redevelop artery-blockage (restenosis) by 6 months), and is responsible for recurrence of symptoms (or death), often requiring repeat revascularization surgery. Despite over a decade of research and significant improvements in the primary success rate of the various medical and surgical treatments of atherosclerotic disease, including angioplasty, bypass grafting and endarterectomy, secondary failure due to late restenosis continues to occur in 30–50% of patients.

The most effective way to prevent this disease is at the cellular level, as opposed to repeated revascularization surgery which can carry a significant risk of complications or death, consumes time and money, and is inconvenient to the patient. In one procedure, the compounds of the present invention can be used as coatings on vascular stents or grants in the procedure outlined in WIPO Publication No. WO 03/020331. Coated stents or grafts can be used in the initial surgery to prevent restenosis from occurring.

As used herein, the following terms in quotations shall have the indicated meanings, whether in plural or singular form:

"Amino acid acyl group" is an acyl group derived from an amino acid. The amino acids may be enumerated by α-amino acids, β-amino acids and tamino acids. Examples of preferred amino acids include glycine, alanine, leucine, senne, lysine, glutamic acid, asparatic acid, threonine, valine, isoleucine, ornithine, glutamine, asparagines, tyrosine, phenylalanine, cysteine, methionine, arginine, β-alanine, tryptophan, proline, histidine, etc. The preferred amino acid is serine and the preferred amino acid acyl group is a serinamide.

"Amine" refers to a free amine $NE_2$ or a lower alkylamino.

"Animal" refers to any warm-blooded mammal, preferably a human.

"Alkyl" refers to a group containing from 1 to 8 carbon atoms and may be straight chained or branched. An alkyl group is an optionally-substituted straight, branched or cyclic saturated hydrocarbon group. When substituted, alkyl groups may be substituted with up to four substituent groups, R, as defined, at any available point of attachment. When the alkyl group is said to be substituted with an alkyl group, this is used interchangeably with "branched alkyl group". Exemplary unsubstituted such groups include methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, and the like. Exemplary substituents may include but are not limited to one or more of the following groups: halo (such as F, Cl, Br, I), haloalkyl (such as $CCl_3$ or $CF_3$), alkoxy, alkylthio, hydroxy, carboxy (—COOH), alkyloxycarbonyl (—C(O)R), alkylcarbonyloxy (—OCOR), amino (—$NH_2$), carbamoyl (—NHCOOR— or —OCONHR—), urea (—NHCONHR—) or thiol (—SH). Alkyl groups as defined may also comprise one or more carbon to carbon double bonds or one or more carbon to carbon triple bonds.

"Aryl" refers to groups with aromaticity, including 5- and 6-membered single-ring aromatic groups that may include from zero to four heteroatoms, as well as multicyclic systems with at least one aromatic ring. Examples of aryl groups include benzene, phenyl, pyrrole, furan, thiophene, thiazole, isothiazole, imidazole, triazole, tetrazole, pyrazole, oxazole, isooxazole, pyridine, pyrazine, pyridazine, and pyrimidine, and the like. The aromatic ring can be substituted at one or more ring positions with such substituents as described above, as for example, halogen, hydroxyl, alkoxy, etc. The preferred aryl group of the present invention is a benzene ring.

"Aroyl" refers to the —(C=O)-aryl groups, wherein aryl is defined as hereinabove. The aryl group is bonded to the core compound through a carbonyl bridge.

"Cycloalkyl" is a species of alkyl containing from 3 to 15 carbon atoms, without alternating or resonating double bonds between carbon atoms. It may contain from 1 to 4 rings. Exemplary unsubstituted such groups include cyclopropyl, cyclobutyl, cyclopentyl, cyclohexyl, adamantyl, etc. Exemplary substituents include one or more of the following groups: halogen, alkyl, alkoxy, alkyl hydroxy, amino, nitro, cyano, thiol and/or alkylthio.

"Halogen" or "Halo" refers to chlorine, bromine, fluorine or iodine.

"Lower alkoxy" refers to —O-alkyl groups, wherein alkyl is as defined hereinabove. The alkoxy group is bonded to the core compound through the oxygen bridge. The alkoxy group may be straight chained or branched; although the straight-chain is preferred. Examples include methoxy, ethyloxy, propoxy, butyloxy, t-butyloxy, i-propoxy, and the like. Preferred alkoxy groups contain 1–4 carbon atoms, especially preferred alkoxy groups contain 1–3 carbon atoms. The most preferred alkoxy group is methoxy.

"Lower alkylamino" refers to a group wherein one or two alkyl groups is bonded to an amino nitrogen, i.e., NH(alkyl). The nitrogen is the bridge connecting the alkyl group the core compound. Examples include NHMe, NHEt, NHPr, and the like.

"Prodrug" refers to a precursor form of the drug which is metabolically converted in vivo to produce the active drug. Preferred prodrugs of the present invention include the phosphate, phosphoramidate, or amino acid acyl groups as defined herein. The phosphate ester salt moiety may also include (—OP(O)(O-Alkyl)$_2$) or (—OP(O)(O$^-$M$^+$)$_2$), wherein M is a cationic salt.

"Phenolic moiety" means herein a hydroxy group when it refers to an R group on an aryl ring.

"Phosphate", "Phosphate moiety", or "Phosphate prodrug salt" refers to phosphate ester salt moiety (—OP(O)(O$^-$M$^+$)$_2$), a phosphate triester moiety (—OP(O)(OR)$_2$) or a phosphate diester moiety (—OP(O)(OR)(O$^-$M$^+$), where M is a salt and R is chosen to be any appropriate alkyl or branched alkyl substituent (the two R groups may be the same alkyl group or may be mixed), or benzyl, or aryl groups. The salt M is advantageously Na, K and Li, but the invention is not limited in this respect.

"Phosphoramidate" refers to a phosphoamidate ester salt moiety (—NP(O)(O$^-$M$^+$)$_2$), a phosphoramidate diester moiety (—NP(O)(OR)$_2$), or a phosphoamidate disalt moiety (—NP(O)(OR)(O$^-$M$^+$), where M is a salt and R is chosen to be any appropriate alkyl or branched alkyl substituent (the two R groups may be the same alkyl group or may be mixed), or benzyl, or aryl groups. The salt M is advantageously Na, K and Li, but the invention is not limited in this respect.

"Salt" is a pharmaceutically acceptable salt and can include acid addition salts such as the hydrochlorides, hydrobromides, phosphates, sulphates, hydrogen sulphates, alkylsulphonates, arylsulphonates, acetates, benzoates, citrates, maleates, fumarates, succinates, lactates, and tartrates; alkali metal cations such as Na, K, Li, alkali earth metal salts such as Mg or Ca or organic amine salts such as those disclosed in PCT International Application Nos. WO02/22626 or WO00/48606.

"Tubulin Binding Agent" shall refer to a ligand of tubulin or a compound capable of binding to either α or β-tubulin, αβ-heterodimers, or microtubules and interfering with the polymerization or depolymerization of microtubules.

"Tumor", "Cancer", or "Neoplastic Disease" shall be used interchangeably and include (but are not limited to) the following:

1) carcinomas, including that of the bladder, breast, colon, kidney, liver, lung, including small cell lung cancer, esophagus, gall bladder, ovary, pancreas, stomach, cervix, thyroid, prostate, and skin, including squamous cell carcinoma;

2) hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma and Burkett's lymphoma;

3) hematopoietic tumors of mycloid lineage, including acute and chronic myelogenous leukemias, myelodysplastic syndrome and promyelocytic leukemia;

4) tumors of mesenchymal origin, including fibrosarcoma and rhabdomyosarcoma;
5) tumors of the central and peripheral nervous system, including astrocytoma, neuroblastoma, glioma and schwannomas; and
6) other tumors, including melanoma, seminoma, teratocarcinoma, osteosarcoma, xenoderoma pigmentosum, keratoctanthoma, thyroid follicular cancer, anaplastic thyroid cancer and Kaposi's sarcoma.

"Vascular toxicity" refers to the selective destruction, damage, or occlusion, whether reversible or irreversible, partial or complete, of proliferating vasculature.

"Malignant proliferating vasculature" refers to the endothelium, artery, blood vessel, or neovasculature formed by a malignant disease state, such as a tumor.

"Nonmalignant proliferating vasculature" refers to the endothelium, artery, blood vessel, or neovasculature formed by undesirable or pathological angiogenesis and that is associated with disease states other than a malignant disease state, including without limitation ocular diseases such wet or age-related macular degeneration, diabetic retinopathy, retinopathy of prematurity, diabetic molecular edema, uveitis, and corneal neovascularization, or other nonocular disease states such as psoriasis, rheumatoid arthritis, atheroma, restenosis, Kaposi's sarcoma, haemangioma, and in general, inflammatory diseases characterized by vascular proliferation.

"Antiproliferative" or "antimitotic" refer to the ability of the compounds of the present invention to directly inhibit the proliferation of tumor cells and impart direct cytotoxicity towards tumor cells through their effect on tumor cell division.

"Treating" (or "treat") as used herein includes its generally accepted meaning which encompasses prohibiting, preventing, restraining, and slowing, stopping, or reversing progression, severity, of a resultant symptom. As such, the methods of this invention encompass both therapeutic and prophylactic administration.

"Effective amount" refers to the amount or dose of the compound, upon single or multiple dose administration to the patient, which provides the desired effect in the patient under diagnosis or treatment.

An effective amount can be readily determined by the attending diagnostician, as one skilled in the art, by the use of known techniques and by observing results obtained under analogous circumstances. In determining the effective amount or dose of compound administered, a number of factors are considered by the attending diagnostician, including, but not limited to: the species of mammal; its size, age, and general health; the specific disease involved,; the degree of or involvement or the severity of the disease; the response of the individual patient; the particular compound administered; the mode of administration; the bioavailability characteristics of the preparation administered; the dose regimen selected; the use of concomitant medication; and other relevant circumstances.

A typical daily dose will contain from about 0.1 mg/kg to about 1000 mg/kg of the active compound of this invention. Preferably, daily doses will be about 10 mg/kg to about 100 mg/kg, and most preferably about 10 mg.

In effecting treatment of a patient afflicted with a condition, disease or disorder described herein, a compound of the present invention can be administered systemically in any form or mode which makes the compound bioavailable in effective amounts. Systemic administration may be accomplished by administration of a compound of the present invention into the bloodstream at a site which is separated by a measurable distance from the diseased or affected organ or tissue. For example, compounds of the present invention can be administered orally, parenterally, subcutaneously, intramuscularly, intravenously, transdermally, intranasally, rectally, buccally, and the like. Oral or intravenous administration is generally preferred for treating neoplastic disease or cancer. Alternatively, the compound may be administered non-systemically by local administration of the compound of the present invention directly at the diseased or affected organ or tissue. Treatment of ocular diseases characterized by the presence of non-malignant proliferative vasculature or neovascularization, can be achieved using non-systemic administration methods such as intravitreal injection, sub-Tenon's injection, ophthalmic drops, iontophoresis, topical formulation and implants and/or inserts. One skilled in the art of preparing formulations can readily select the proper form and mode of administration depending upon the particular characteristics of the compound selected, the disease state to be treated, the stage of the disease, and other relevant circumstances.

It will be understood by the skilled reader that all of the compounds used in the present invention are capable of forming salts, and that the salt forms of pharmaceuticals are commonly used, often because they are more readily crystallized and purified than are the free bases. In all cases, the use of the pharmaceuticals described above as salts is contemplated in the description herein, and often is preferred, and the pharmaceutically acceptable salts of all of the compounds are includes in the names of them.

According to another aspect, the present invention provides a pharmaceutical composition, which comprises a compound of the present invention or a pharmaceutically acceptable salt thereof as defined hereinabove and a pharmaceutically acceptable diluent or carrier.

The pharmaceutical compositions are prepared by known procedures using well-known and readily available ingredients. In making the compositions of the present invention, the active ingredient will usually be mixed with a carrier, or diluted by a carrier, or enclosed within a carrier, and may be in the form of a capsule, sachet, paper, or other container. When the carrier serves as a diluent, it maybe a solid, semi-solid, or liquid material which acts as a vehicle, excipient, or medium for the active ingredient. The compositions can be in the form of tablets, pills, powders, lozenges, sachets, cachets, elixirs, suspensions, emulsions, solutions, syrups, aerosols, ointments containing, for example, up to 10% by weight of active compound, soft and hard gelatin capsules, suppositories, sterile injectable solutions, and sterile packaged powders.

Some examples of suitable carriers, excipients, and diluents include lactose, dextrose, sucrose, sorbitol, mannitol, starches, gum, acacia, calcium phosphate, alginates, tragcanth, gelatin, calcium silicate, micro-crystalline cellulose, polyvinylpyrrolidone, cellulose, water syrup, methyl cellulose, methyl and propyl hydroxybenzoates, talc, magnesium stearate, and mineral oil. The formulations can additionally include lubricating agents, wetting agents, emulsifying and suspending agents, preserving agents, sweetening agents, or flavoring agents. Compositions of the invention may be formulated so as to provide quick, sustained, or delayed release of the active ingredient after administration to the patient by employing procedures well know in the art.

The compositions are preferably formulated in a unite dosage form, each dosage containing from about 1 mg to about 500 mg, more preferably about 5 mg to about 300 mg (for example 25 mg) of the active ingredient. The term "unit dosage form" refers to a physically discrete unit suitable as unitary dosages for human subjects and other mammals, each unit containing a predetermined quantity of active material calculated to produce the desired therapeutic effect, in association with a suitable pharmaceutical carrier, diluent, or excipient. The following formulation examples are illustrative only and are not intended to limit the scope of the invention in any way.

The compositions of the present invention may be formulated in a conventional manner using one or more pharmaceutically acceptable carriers. Thus, the active compounds of the invention may be formulated for oral, buccal, transdermal (e.g., patch), intranasal, parenteral (e.g., intravenous, intramuscular or subcutaneous) or rectal administration or in a form suitable for administration by inhalation or insufflation.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose of calcium phosphate); lubricants (e.g., magnesium stearate, talc or silica); disintegrants (e.g., potato starch or sodium starch glycollate); or wetting agents (e.g., sodium lauryl sulphate). The tablets may be coated by methods well known in the art. Liquid preparations for oral administration may take the form, of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); and preservatives (e.g., methyl or propyl p-hydroxybenzoates or sorbic acid).

For buccal administration the composition may take the form of tablets or lozenges formulated in conventional manner.

The active compounds of the invention may be formulated for parenteral administration by injection, including using conventional catheterization techniques or infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulating agents such as suspending, stabilizing and/or dispersing agents. Alternatively, the active ingredient may be in a powder form for reconstitution with a suitable vehicle, e.g., sterile pyrogen-free water, before use.

The active compounds of the invention may also be formulated in rectal compositions such as suppositories or retention enemas, e.g., containing conventional suppository bases such as cocoa butter or other glycerides.

For intranasal administration or administration by inhalation, the active compounds of the invention are conveniently delivered in the form of a solution or suspension form a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the invention and a suitable powder base such as lactose or starch.

Tablets or capsules of the compounds may be administered singly or two or more at a time as appropriate. It is also possible to administer the compounds in sustained release formulations.

The physician will determine the actual dosage which will be most suitable for an individual patient and it will vary with the age, weight and response of the particular patient. The above dosages are exemplary of the average case. There can of course, be individual instances where higher or lower dosage ranges are merited, and such are within the scope of this invention.

The compounds of the present invention can be administered by inhalation or in the form of a suppository or pessary, or they may be applied topically in the form of a lotion, solution, cream, ointment or dusting powder. An alternative means of transdermal administration is by use of a skin patch. For example, they can be incorporated into a cream consisting of an aqueous emulsion of polyethylene glycols or liquid paraffin. They can also be incorporated, at a concentration of between 1 and 10% by weight, into an ointment consisting of a white wax or white soft paraffin base together with such stabilizers an preservatives as may be required.

"Administering" means any of the standard methods of administering a compound to a subject, known to those skilled in the art. Examples include, but are not limited to intravenous, intramuscular or intraperitoneal administration.

For the purposes of this invention "pharmaceutically acceptable carriers" means any of the standard pharmaceutical carriers. Examples of suitable carriers are well known in the art and may include, but are not limited to, any of the standard pharmaceutical carriers such as a phosphate buffered saline solutions phosphate buffered saline containing Polysorb 80, water, emulsions such as oilwater emulsion, and various type of wetting agents. Other carrier may also include sterile solutions, tablets, coated tablets, and capsules.

Typically such carriers contain excipients such as starch, milk, sugar, certain types of clay gelatin, stearic acid or salts thereof, magnesium or calcium stearate, talc, vegetable fats or oils, gums glycols, or other known excipients. Such carriers may also include flavor and color additives or other ingredients. Compositions comprising such carriers are formulated by well known convention methods.

Methods of determining an "effective amount" are well known to those skilled in the art and depend upon factors including, but not limited to: the size of the patient and the carrier used.

The invention is further defined by reference to the following examples and preparations which describe the manner and process of making and using the invention and are illustrative rather than limiting. It will be apparent to those skilled in the art that many modifications, both to the materials and methods, may be practiced without departing from the purpose and interest of the invention.

EXAMPLES

Materials and Methods

Chemicals were obtained commercially from the Aldrich Chemical Company, Fisher Scientific, and ACROS Chemicals and used directly as purchased. Solvents such as ethylacetate, acetone, and diethyl ether, were used as purchased, and others were purified by standard procedures as necessary. Methylene chloride ($CH_2Cl_2$) was dried over calcium hydride and distilled immediately prior to use. Hexanes were distilled prior to use.

Reactions were followed by thin layer chromatography (TLC), and/or gas chromatography mass spectrometry (GC-MS). Products were purified using flash column chromatography with silica gel (260–400 mesh), preparatory thin layer chromatography or recrystillization. Silica gel plates for thin layer chromatogiaphy (TLC), preparatory chromatography, and silica gel (200–400 mesh) for column chromatography were obtained from Merck EM Science.

Proton ($^1H$), carbon ($^{13}C$), phosphorus ($^{31}P$) NMR was obtained at 300 MHZ, 75 MHZ, and 120 MHZ, respectively, in the solvent indicated. Chemical shifts are expressed in ppm (δ), peaks are listed as singlet (s) doublet (d), triplet (t) or multiplet (m), with coupling constant (J) expressed in Hz.

Elemental analyses were obtained from Atlantic Microlab Inc., Norcross, Ga. Melting points were determined using a Thomas-Hoover melting point apparatus and are uncorrected.

Example 1

Large-scale Preparations of Tribromosiloxy (TBSO) Protected Mono-Bromide as a Starting Material for Synthesis of Tubulin Binding Agents The following reactions are illustrated in FIG. 1:

3-tert-butyldimethylsiloxy (TBSO)-4-methoxybenzaldehyde (1).

To a 1-L round-bottom flask was added Isovanillin (80 g, 526 mol) and DMAP (1 g) under inert atmosphere. Dry dichloromethane (~450 mL) was added, followed by triethylamine (81 mL, 580 mol), at which point the solid entirely dissolved. The mixture was cooled to 0° C. and tert-butyldimethylsilyl ("TBS") chloride ("TBSCl", 89 g, 590 mol) was added in one portion. The mixture began almost immediately to precipitate solid. The mixture was allowed to stir for 1.5 h at 0° C., at which point TLC (30% EtOAc/hexanes) showed an almost complete absence of isovanillin. The mixture was allowed to stir overnight, then the precipitate was filtered off through Celite. The filtrate was washed with water (200 mL) followed by saturated NaCl solution (200 mL) and dried over MgSO4. This was filtered into a tared 1-L flask and concentrated by distillation on a rotary evaporator, followed by aspirator vacuum to approximately constant weight, yielding a deep red-brown liquid (149.4 g; theoretical=140 g). This material was taken into the next reaction without further characterization.

1-(3-tert-butyldimethylsiloxy(TBSO)-4-methoxyphenyl) ethanol (2).

The entire crude product from the preceding reaction (~526 mol) was transferred as a solution in dry ether (200 mL) to a 2-L round bottom flask equipped with a very large magnetic stirring bar. An additional 500 mL of dry ether were added and the mixture was cooled to 0° C. Then methyllithium (500 mL of a 1.4 M solution, 700 mol) was added over ~40 minutes by cannula, and the mixture was allowed to stir overnight. The deep red mixture was re-cooled to 0° C. and treated with water (200 mL) very cautiously at first. The mixture became a heterogeneous yellow. In a separatory funnel, the aqueous phase was separated and the organic phase was washed once with saturated NaCl solution and dried over MgSO4. After filtration and concentration by distillation on a rotary evaporator followed by aspirator vacuum, a deep red liquid was obtained (136.8 g), and was found to be free of starting material by TLC. This material was taken into the next reaction without further characterization.

3-tert-butyldimethylsiloxy(TBSO)-4-methoxyacetophenone (3).

The entire amount of the crude alcohol from the preceding reaction was transferred to a 3-L round bottom flask as a solution in ~1.5 L of dry dichloromethane. Celite (62 g, oven dried), $K_2CO_3$ (16 g) and a very large magnetic stirring bar were added. PCC (115 g) was then added in portions over a 2-hr period, during which time the heterogeneous yellow mixture became dark brown. At the end of the addition, large amounts of the starting alcohol were still present by TLC (25% EtOAc/hexanes) so the mixture was allowed to stir overnight. At this point, the starting alcohol was absent (or nearly so) by TLC, and the mixture was filtered through a 3-cm pad of silica gel, rinsing well with dichloromethane. The mud-brown solution was concentrated by distillation on a rotary evaporator followed by aspirator vacuum to yield an opaque brown liquid. This was purified in 30 mL portions by Kugelrohr distillation (~0.5 Torr, 140° C.) to yield 104.4 g of a brown liquid which crystallized on brief standing. This was dissolved in hot hexanes (104 mL) and filtered hot through Celite to yield a clear yellow solution. This was seeded and left in a refrigerator (~5° C.) overnight. The crystalline product was filtered cold, washed quickly with a small amount of cold hexanes and dried under pump vacuum to give 84.8 g (303 mol, 58% yield from isovanillin) recrystallized light yellow solid, pure by $^1H$ and $^{13}C$ NMR. A second crop of crystals (6.3 g) were obtained by dissolving the concentrated filtrate in hot hexanes (20 mL) followed by seeding and standing overnight.

3. $^1H$ NMR ($CDCl_3$): 0.15 (s, 6H); 0.98 (s, 9H); 2.52 (s, 3H); 3.85 (s, 3H); 6.85 (d, 1H, J=8.4); 7.45 (s, 1H); 7.56 (dd, 1H, J=8.4, 2.2). $^{13}C$ NMR ($CDCl_3$): –4.8, 18.4, 25.6, 26.3, 55.4, 110.7, 120.2, 123.5, 130.5, 144.7, 155.3, 196.8.

α-halo-3-tert-butyldimethylsiloxy(TBSO)-4-methoxyacetophenone (5)

An important part of the present invention is a new efficient method of converting 3-TBSO-4-methoxyacetophenone (3) to α-halo-3-TBSO-4-methoxyacetophenone (5) by treatment of the trimethylsilyl enol ether (4) [1-(3-TBSO-4-methoxyphenyl)-1-trimethylsiloxy(TMSO)-ethylene] with elemental halogen. Bromine is the preferred halogen. It is understood that chlorine and iodine may be utilized in place of bromine should iodo or chloro analogs be desired.

Example 2

Figure 2:
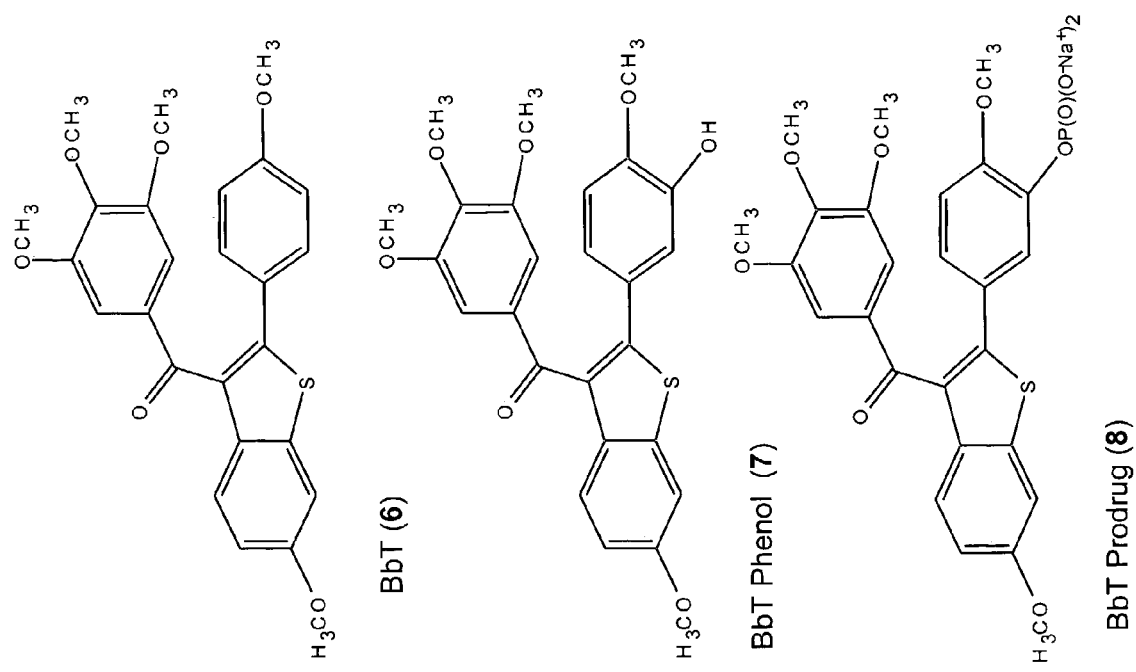
FIG. 2 depicts exemplary benzo[b]thiophene ligands and corresponding prodrug construct.
Figure 3:
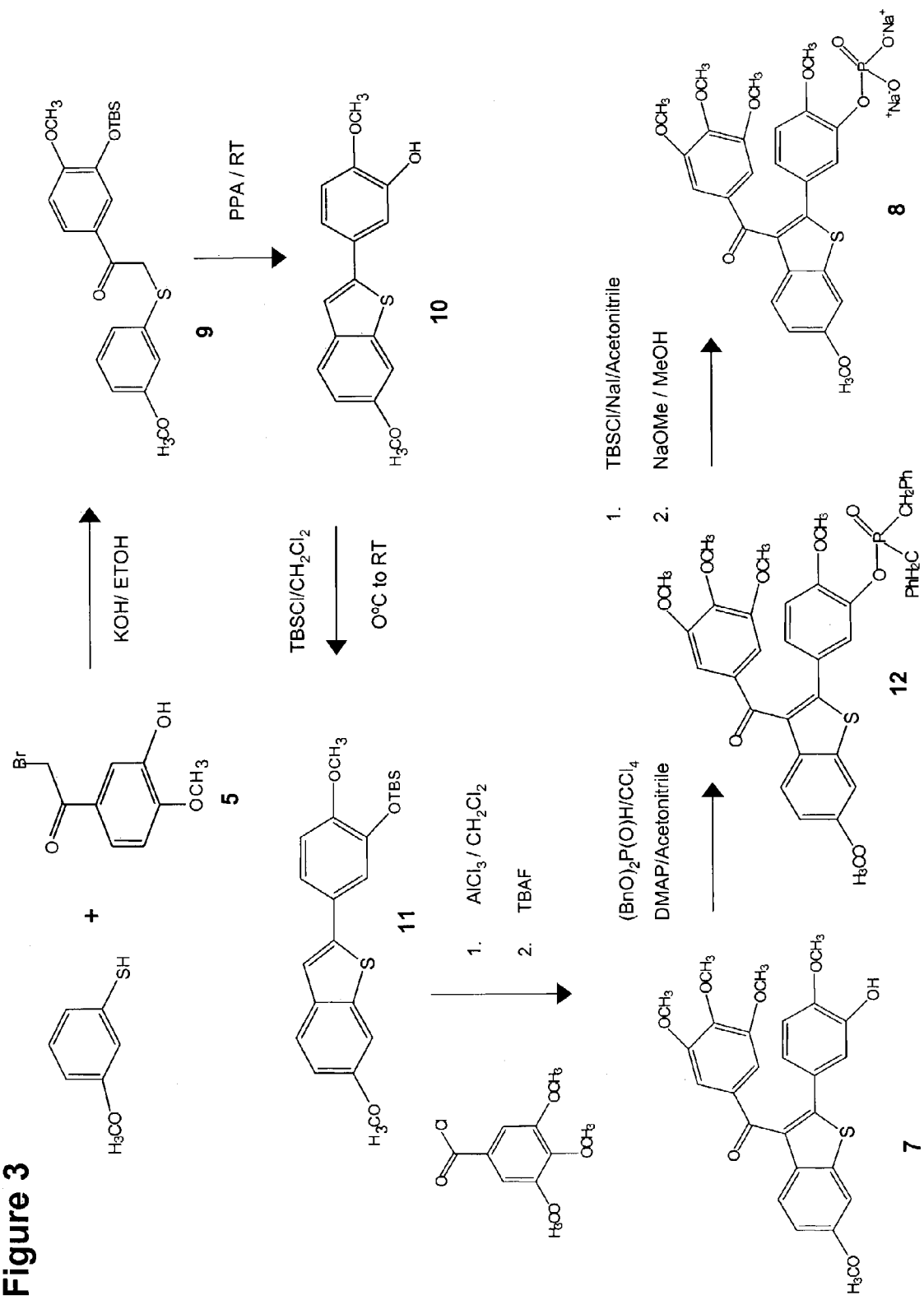
FIG. 3 illustrate the synthesis of an exemplary benzo[b]thiophene prodrug construct.

Synthesis of Benzo[b]thiophene-based Prodrug a. Synthesis of an Aroyl-Substituted Benzo[b]thiophene Phosphate Prodrug Excellent in vitro cytotoxicity shown by the lead compound 6 (FIG. 2) in our benzo[b]thiophene series (Pinney et al, Bioorg. Med. Chem. Lett., 1999), has prompted us to design a prodrug for this lead compound. A route for the synthesis of this prodrug is illustrated in FIG. 3.

Treatment of 5 with 3-methoxybenzene thiol gave a sulfide 9. Cyclization was accomplished by combining sulfide 9 (0.417 g, 0.996 mmol) with polyphosphoric acid ("PPA", 30 g) in a 3 neck round bottom flask with stirring under nitrogen at 30–35° C. After 1 h, the reaction was quenched with ice water followed by work up with $CH_2Cl_2$. The organic layer was washed thoroughly with water and dried over $MgSO_4$. Removal of solvent, followed by purification by column chromatography (80:20 hexanes:EtOAc) afforded para cyclized, deprotected 2-(3'-hydroxy-4'-methoxyphenyl)-6-methoxybenzo[b]thiophene 10 in good yield.

10. (0.252 g, 0.880 mmol, 88%) $^1$H-NMR ($CDCl_3$, 360 MHz) δ 7.80 (d, J=8.87 Hz, 1H, ArH), 7.36 (d, J=2.34 Hz, 1H, ArH), 7.17 (d, J=2.09 Hz, 1H, ArH), 7.16 (s, 1H, Ph-CH=C), 7.07 (dd, J=8.24 Hz, 2.1 Hz, 1H, ArH), 7.01 (dd, J=8.89 Hz, 2.40 Hz, 1H, ArH), 6.95 (d, J=8.28 Hz, 1H, ArH), 5.70 (s, 1H, —OH), 3.96, (s, 3H, —OCH$_3$), 3.89 (s, 3H, —OCH$_3$).

Since cyclization step also caused deprotection of the silyl-protected alcohol, the hydroxy group was re-protected as its corresponding silyl ether by treatment with TBSCl to give 2-(3'-tert-butyldimethylsilyloxy-4'-methoxy phenyl)-6-methoxybenzo[b]thiophene, 11. Friedel-Craft's acylation of 11 (0.105 g, 0.262 mmol) with 3,4,5-trimethoxybenzoyl chloride at 0° C. under nitrogen followed by $AlCl_3$ (0.112 g, 0.839 mmol). The reaction mixture was brought to RT and stirred for 1.5 h. The reaction was then quenched with water followed by extraction with $CH_2Cl_2$. The organic layer was washed with brine and dried over $MgSO_4$. Solvent removal followed by purification by column chromatography (gradual increase in polarity of the solvent from 90%, 80%, 50% Hexanes: EtOAc mixture) afforded the TBS-protected BbT phenol (0.127 g, 0.226 mmol, 86%) as a yellow colored oil. A small amount of deprotected BbT phenol 7 was observed as well. Deprotection with tert-butylammonium fluoride ("TBAF",1M in THF, 0.350 mL, 0.350 mmol) was accomplished in $CH_2Cl_2$ (10 mL) at 0° C. under nitrogen. The reaction mixture was brought to room temperature and stirred for 1 hr. The reaction mixture was then quenched with water followed by the usual work-up (EtOAc, brine, and drying over $MgSO_4$). Removal of solvent followed by purification by column chromato-graphy, resulted in exclusive formation of the BbT phenol, 3-(3',4',5'-trimethoxybenzoyl)-2-(3'-hydroxy-4'-methoxyphenyl)-6-methoxybenzo[b]thiophene, 7, as a yellow colored solid.

Oxi-com 139, 7. (0.049 g, 0.102 mmol, 45%)

$^1$H-NMR ($CDCl_3$, 360 MHz) δ 7.71 (d, J=9.01 Hz, 1H, ArH), 7.36 (d, J=2.29 Hz, 1H, ArH), 7.03 (dd, J=2.38 Hz, 9.01 Hz, 1H, ArH), 6.89 (d, J 1.99 Hz, 1H, ArH), 6.86 (s, 2H, ArH), 6.70 (dd, J=1.99 Hz, 8.21 Hz, 1H, ArH), 6.65 (d, J=8.22 Hz, 1H, ArH), 5.57 (s, 1H, OH), 3.93 (s, 3H, —OCH$_3$), 3.83 (s, 3H, —OCH$_3$), 3.79 (s, 3H, —OCH$_3$), 3.77 (s, 6H, —OCH$_3$).

$^{13}$C-NMR ($CDCl_3$, 75 MHz) δ 190.4, 159.5, 152.4, 146.4, 145.2, 142.8, 141.3, 141.2, 135.2, 133.2, 127.8, 126.2, 122.5, 116.2, 115.8, 110.3, 106.9, 104.2, 60.7, 56.0, 55.9, 55.7. HRMS (EI) M$^+$ calcd for $C_{26}H_{24}O_7S$ 480.1243, found 452.1230. Anal. calcd for $C_{26}H_{24}O_7S$: C, 64.99; H, 5.03; S, 6.67. Found: C,64.85; H, 5.15; S, 6.58.

Phosphorylation of 7 (0.037 g, 0.077 mmol) was accomplished under $N_2$ in acetonitrile (1 mL) at −25° C. by adding $CCl_4$ (1 mL). After stirring for 10 min, ethyldiisopropylamine (0.030 mL, 0.164 mmol) and DMAP (0.010 g) were added. Dibenzylphosphite (0.030 mL, 0.136 mmol) was added after 5 min and the mixture was stirred at −20° C. for 1.5 h. The reaction mixture was slowly warmed to room temperature and stirred for an additional 2 h at which time $KH_2PO_4$ was added and the product was isolated by extraction with EtOAc. The organic layer was washed with water and brine, and dried over $MgSO_4$. Following solvent evaporation, purification by column chromatography (gradual increase of solvent polarity from 70% to 60% hexanes: EtOAc) yielded the desired dibenzylphosphate 12 as a yellowish-white thick liquid.

12. (0.031 g, 0.042 mmol, 55%) $^1$H-NMR ($CDCl_3$, 360 MHz) δ 7.63 (dd, J=9.01 Hz, 0.34 Hz, 1H, ArH), 7.35 (d, J=2.24 Hz, 1H, ArH), 7.29 (m, 10H, ArH), 7.19 (dd, J=2.06 Hz, 1H, 2.05 Hz, ArH), 7.04 (ddd, J=8.41 Hz, 2.11 Hz, 2.10 Hz, 1H, ArH),7.00 (dd, 9.01 Hz, 2.38 Hz, 1H, ArH), 6.87 (s, 2H, ArH), 6.78 (dd, J=8.51 Hz, 0.85 Hz, 1H, ArH), 5.14 (d, J=8.06 Hz, 4H, —CH$_2$), 3.93 (s, 3H, —OCH$_3$), 3.79 (s, 3H, —OCH$_3$), 3.75 (s, 3H, —OCH$_3$), 3.73 (s, 6H, —OCH$_3$). $^{31}$P-NMR ($CDCl_3$, 145 MHz) δ(−5.34). LRMS (EI) M$^+$ found for $C_{40}H_{37}O_{10}SP$: 740.534.

To a well-stirred solution of dibenzyl ester 12 (0.100 g, 0.141 mmol) in dry acetonitrile (6 mL) was added sodium iodide (0.0423 g, 0.282 mmol). Chlorotrimethylsilane (0.03 g, 0.024 mL, 0.282 mmol) was slowly added to this solution. After 30 min, water was slowly added until all of the visible salts were dissolved. The straw color was removed upon the addition of a sodium thiosulphate (10%) solution. The organic phase was separated, and the aqueous phase was extracted with ethyl acetate (4×50 mL). The combined organic layer was concentrated in vacuo to give a pale yellow foam which was dissolved in dry methanol (5 mL). To this solution was added sodium methoxide (0.0152 g, 0.282 mmol) in one portion. After stirring for 9 h, the methanol was removed in vacuo and the resultant solid was recrystallized from $H_2O$/acetone to afford the disodium salt 3-(3',4',5'-trimethoxybenzoyl)-2-(3'-sodiumphosphate-4'-methoxyphenyl)-6-methoxybenzo[b]thiophene, 8 as a pale yellow powder.

8. (0.040 g, 0.066 mmol, 47%) $^1$H-NMR (DMSO, 300 MHz) δ 3.62 (s, 3H),3.66 (s, 3H), 3.70 (s, 6H), 3.89 (s, 3H), 6.67 (m, 2H), 6.80 (s, 2H), 7.15 (d, J=11.1 Hz, 1H), 7.69 (m, 2H), 7,84 (d, J=11.1, 1H). $^{13}$C-NMR (DMSO, 75 MHz) δ 56.3, 56.5, 56.7, 60.8, 105.7, 107.4, 112.6, 116.7, 122.4, 124.4, 126.6, 127.3, 133.5, 133.7, 134.9, 141.5, 142.5, 142.8, 144.4, 144.5, 150.5, 150.6, 152.9, 160.0, 190.7. $^{31}$P-NMR (DMSO, 300 MHz) δ−1.94

Following a very similar methodology, one skilled in the art can readily prepare a wide variety of other phosphate prodrug constructs containing other metals salts or alkyl groups, or nitrogen based phosphoramidates, amino acyl prodrug, and their corresponding salts.

b. Synthesis of an Aryloxy Ether-substituted Benzo[b] thiophene Prodrug

We have previously described a benzo[b]thiophene aryloxy ether based compounds (PCT publication WO 98/39323; Pinney et al., J. Org. Chem, 2000) in which the carbonyl group Aroyl-substituted BbT has been replaced with an oxygen atom. Since these compounds demonstrate strong cytotoxicity and excellent inhibition of tubulin polymerization, a natural extension is the preparation of phosphate and phosphoramidate prodrugs following a synthetic protocol similar to that established in FIG. 3.

c. Synthesis of 2,3-Diarylbenzo[b]thiophene Prodrugs

Figure 4:
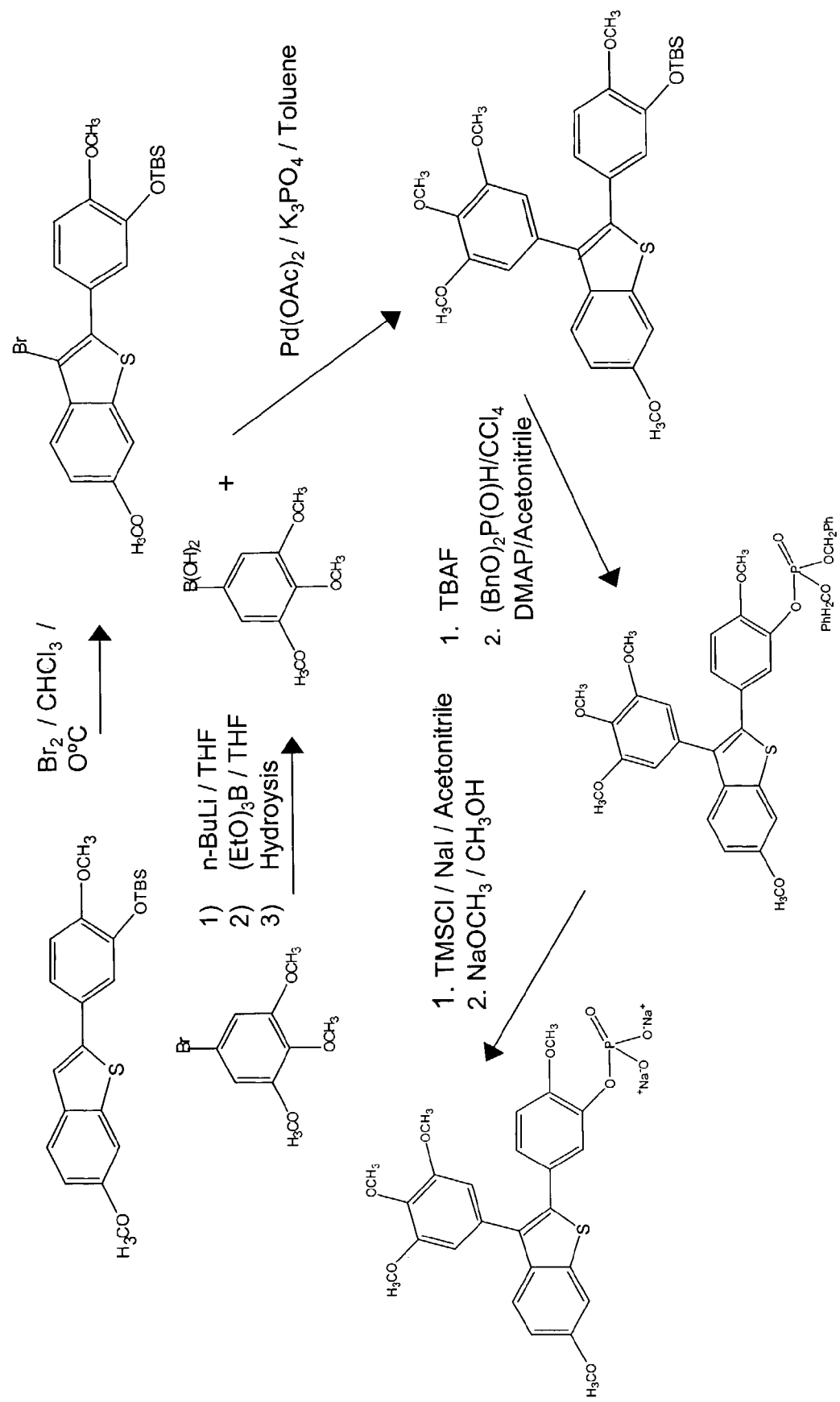
FIG. 4 illustrates the synthesis of an exemplary 2,3-diarylbenzo[b]thiophene prodrug construct.

A representative synthesis, which utilized a Suzuki coupling reaction as a key synthetic step, is illustrated in FIG. 4. A very similar methodology can be employed by persons skilled in the art to prepare related compounds which vary in the position and number of phenolic moieties and phosphate prodrug moieties and/or amine groups and phosphoramidate groups around the core diarylbenzo[b]thiophene ring system. It should be noted that the phenolic precursor to one of these compounds has recently been prepared (Flynn B E, et al., Organic Letters, 2001, 3: 651–654) but no mention has been made of the corresponding prodrug constructs.

Example 3

Figure 5:
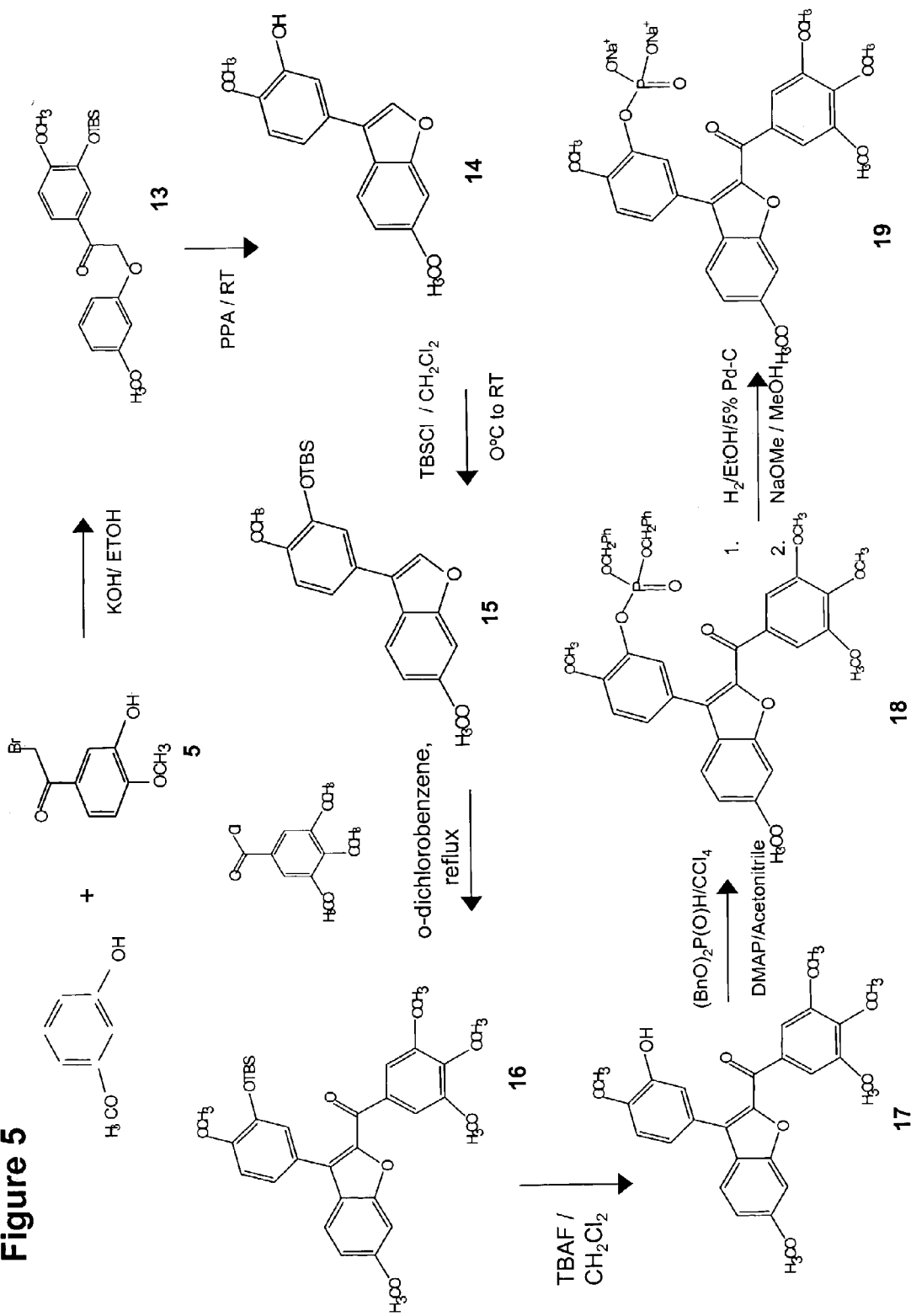
FIG. 5 illustrates the synthesis of an exemplary benzo[b]furan monophosphate prodrug construct.

Benzofuran Based Prodrugs a. Synthesis of Diaryl-substituted, Monophosphate Benzofuran Based Prodrugs A variety of Aryl-substituted benzofuran derivatives have been previously described by the inventors (PCT publication WO 98/39323). Based on the other prodrug constructs hereinbefore described, the preparation of diaryl-substituted benzo[b]furans and corresponding phosphate and phosphoramidate prodrugs of the benzofuran ring skeleton are also provided. An exemplary diaryl-BbF 13 and its corresponding disodium phosphate prodrug 14 have been synthesized as illustrated in FIG. 5. It is important to note that the substitution patterns of phosphate and phosphoramidate at the C-3' position on the pendant aryl ring of the benzofuran can alternatively be contained at other aryl positions, most notably C-5' and C-7'.

3-[(tert-]-Butyldimethylsilyl]oxy-4-methoxy-alpha-[(3-methoxyphenyl)oxy]acetophenone, 13

To a solution of KOH (1.66 g, 29.6 mmol) in EtOH (16 mL) and H$_2$O (8 mL) was added 3-methoxyphenol (3.30 mL, 29.6 mmol) at 0° C. After stirring for 10 min bromoacetophenone 5(7.10 g, mmol) in EtOAc (8 mL) was added in a dropwise fashion. The reaction mixture was stirred for 12 h allowing to reach room temperature. The reaction mixture was quenched with water, the phases separated, and the aqueous phase extracted with EtOAc (3×100 mL). The combined organic solutions were dried over MgSO$_4$ and concentrated under reduced pressure. Purification by flash column chromatography (silica gel, elution with Hexanes/EtOAc: 90/10) yielded 9.91 g (24.6 mmol, 80%) of ether 13 as a dark oil.

3-(3'-hydroxy-4'-methoxyphenyl)-6-methoxybenzo[b]furan 14

To ether 13 (6.51 g, 16.1 mmol), in a three neck round bottom flask, was added PPA (97.5 g) and stirred (mechanically) under nitrogen at room temperature for 2 hours. The reaction was quenched with ice water, the phases separated, and the aqueous layer was extracted with EtOAc (3×150 mL). The combined organic phases were dried over MgSO$_4$ and concentrated under reduced pressure. Purification by flash column chromatography (silica gel, elution with hexanes/EtOAc:70/30) provided 3.5 g (12.96 mmol, 70%) of hydroxyl ligand 14 as a white solid.

$^1$H-NMR (CDCl$_3$, 300 MHz) δ 3.87 (s, 3H); 3.94 (s, 3H); 5.69 (s, 1H) 6.93 (dd, J=2.2, 8.6 1H); 6.94 (d, J=8.2, 1H); 7.05 (d, J=2.2, 1H); 7.13 (dd, J=2.1, 8.2, 1H); 7.20 (d, J=2.1, 1H); 7.64 (s, 1H) 7.68 (d, J=8.6, 1H). $^{13}$C-NMR (CDCl$_3$, 75 MHz): δ 55.75, 56.07, 96.14, 111.07, 111.95, 113.62, 119.09, 119.94, 120.55, 121.69, 125.58, 139.90, 145.96, 146.05, 156.76, 158.10.

3-(3'-tert-Butyldimethylsilyloxy-4'-methoxyphenyl)-6-methoxybenzo[b]furan 15

To a solution of 14 (3.51 g, 12.9 mmol) in CH$_2$Cl$_2$ (30 mL), under nitrogen, was added Et$_3$N (1.98 mL, 14.2 mmol) followed by DMAP (0.162 g, 14.2 mmol) and TBSCl (2.4 g, 14.2 mmol) at 0° C. The reaction mixture was stirred for 12 h allowing too reach room temperature. The reaction was quenched with water, the phases separated, and the aqueous phase was extracted with CH$_2$Cl$_2$ (3×30 mL). The combined organic solutions were dried over MgSO$_4$ and concentrated under reduced pressure. Purification by flash column chromatography (silica gel, elution with hexanes) afforded 4.57 g (11.9 mmol, 92%) of the protected benzo[b]furan 15 as a colorless oil.

$^1$H-NMR (CDCl$_3$, 300 MHz): δ 0.20 (s, 6H); 1.02 (s, 9H); 3.85 (s, 3H); 3.87 (s, 3H); 6.93 (dd, J=2.1, 8.6, 1H); 6.93 (d, J=8.2, 1H) 7.05 (d, J=2.2, 1H); 7.11 (d, J=2.1, 1H); 7.17 (dd, J=2.2, 8.2, 1H); 7.63 (s, 1H) 7.65 (d, J=8.6, 1H).

3-(3"-tert-Butyldimethylsilyloxy-4"-methoxyphenyl)-6-methoxy-2-(3',4',5'-trimethoxybenzoyl)benzo[b]furan 16

To a solution of 15 (3.51 g, 9.14 mmol), in O-dichlorobenzene (20 mL), under nitrogen, was added 3, 4, 5-trimethoxybenzoylchloride (3.17 g, 13.7 mmol). The reaction mixture was heated to reflux (190° C.) and stirred for 12 hours. Solvent was removed by distillation under reduced pressure. After cooling to room temperature, a dark solid was formed which was dissolved in CH$_2$Cl$_2$. The reaction mixture was washed with sat. NaHCO$_3$, the phases separated, and the aqueous phase was extracted with CH$_2$Cl$_2$ to remove excess 3, 4, 5-trimethoxybenzoylchloride. The combined organic solutions were dried of MgSO$_4$ and concentrated under reduced pressure. Purification by flash column chromatography (elution with hexanes/EtOAc: 60/40) afforded 2.45 g (4.23 mmol, 46%) of the acylated furan 16 as a yellow oil.

$^1$H-NMR (CDCl$_3$, 300 MHz) δ 0.08 (s, 6H); 0.95 (s, 9H); 3.76 (s, 6H); 3.79 (s, 3H); 3.84 (s, 3H); 3.91 (s, 3H); 6.82 (d, J=8.2, 1H); 6.83 (d, J=2.2, 1H); 6.98 (dd, J=2.2, 8.8, 1H); 7.03 (dd, J=2.1, 8.3, 1H); 7.07 (s, 2H); 7.11 (d, J=2.1, 1H); 7.58 (d, J=8.8, 1H). $^{13}$C-NMR (CDCl$_3$, 75 MHz): δ 0.422, 56.14, 56.50, 56.71, 61.42, 96.49, 107.87, 112.52, 113.30, 120.12, 120.81, 121.47, 122.35, 124.57, 125.53, 125.55, 126.21, 140.42, 140.61, 143.05, 151.08, 153.44, 157.15, 158.55, 164.75.

Oxi-com 194, 2-(3"-hydroxy-4"-methoxyphenyl)-6-methoxy-3-(3', 4', 5'-trinzethoxybenzoyl)benzo[b]furan 17

To a solution of 16 (2.45 g, 4.23 mmol) in CH$_2$Cl$_2$ (20 mL), under nitrogen, was added TBAF (1M in THF, 6.35 mL, 6.35 mmol) at 0° C. The reaction mixture was stirred for 15 minutes and allowed to reach room temperature. The reaction mixture was quenched with water (20 mL), the phases separated, and the aqueous phase was extracted with EtOAc (3×30 mL). The combined solutions were dried over Na$_2$SO$_4$ and concentrated under reduced pressure. Purification by flash column chromatography (silica gel, elution with hexanes/EtOAC: 60/40) afforded 1.73 g (3.72 mmol, 88%) of the desired phenol 17 as a yellow colored solid.

$^1$H-NMR (CDCl$_3$, 300 MHz) δ 3.79 (s, 6H); 3.85 (s, 3H); 3.88 (s, 3H); 3.91 (s, 3H); 5.62 (s, 1H); 6.76 (d, J=8.3, 1H); 6.86 (dd, J=2.1, 8.3, 1H); 6.98 (dd, J=2.2, 8.7, 1H); 7.03 (d, J=2.1, 1H); 7.07 (s, 2H); 7.10 (d, J=2.2, 1H); 7.59 (d, J=8.8, 1H).

2-(3"-dibenzylphosphate-4"-methoxyphenyl)-6-methoxy-3-(3',4',5'-trimethoxybenzoyl)benzo[b]furan 18

To a solution of 17 (1.66 g, 3.57 mmol), under nitrogen, in acetonitrile (40 mL) was added CCl$_4$ (3.05 mL, 31.4 mmol) at −25° C. After stirring for 10 min, ethyldiisopropylamine (1.31 mL, 7.50 mmol) and DMAP (0.04 g, 0.36 mmol) were added. Dibenzylphosphite (1.18 mL, 5.36 mmol) was added after 5 min, and the mixture was stirred at −20° C. for 2 hrs. The reaction mixture was slowly warmed to room temperature and stirred for an additional 2 hrs at which point a KH$_2$PO$_4$ solution (10 mL, 0.5M) was added, the product was isolated by extraction with EtOAc (3×30 mL). The combined organic solutions were dried over MgSO$_4$ and concentrated under reduced pressure. Purification by flash column chromatography (silica gel, elution with hexanes/ EtOAc: 50/50) yielded 2.38 g (3.29 mmol, 92%) of the desired dibenzyl phosphate 18 as a colorless oil.

$^1$H-NMR (CDCl$_3$, 300 MHz) δ 3.79 (s, 6H); 3.80 (s, 3H); 3.87 (s, 3H); 3.91 (s, 3H); 5.17 (d, J=7.9, 4H) 6.89 (d, J=8.6, 1H); 6.94 (dd, J 2.2, 8.6, 1H); 7.08 (d, J=2.2, 1H); 7.13 (s, 2H); 7.30 (m, 11H); 7.42 (m, 1H); 7.51 (d, J=8.8, 1H).

Oxi-com 195, 2-(3"-disodiumphosphate-4"-methoxyphenyl)-6-methoxy-3-(3',4',5'-trimethoxybenzoyl)benzo[b]furan 19

To a solution of dibenzyl ester 18 (2.38 g) in 100% ethanol (40 mL), under argon, was added 5% palladium-carbon (1.00 g). The flask was then closed and all air was evacuated by vacuum pump. A balloon filled with H$_2$, a stopcock valve, and a needle was used to add hydrogen to the flask. The flask was then evacuated again and hydrogen gas was passed into the flask again using the hydrogen filled balloon. The reaction proceeded for 2 hrs then checked by reverse phase thin layer chromatography (TLC). The reaction mixture was filtered through a pipet filled with celite and concentrated under reduced pressure to give a greenish-yellow foam. To a solution of the crude phosphate (1.96 g, 3.60 mmol) in dry methanol (15 mL), in a pear-shaped flask, was added sodium methoxide (1.65 mL of a 4.37M solution, 7.2 mmol) and the reaction mixture was kept in the refrigerator. The next day a yellow solid had formed at the bottom of the flask that crystallized from acetone and water as a yellow solid 19.

$^1$H-NMR (CDCl$_3$, 300 MHz) δ 3.61 (s, 9H); 3.73 (s, 3H); 3.74 (s, 3H); 6.45 (m, 1H); 6.58 (d, J=8.4, 1H); 6.70 (s, 2H); 6.82 (m, 1H); 6.92 (m, 1H); 7.45 (m, 1H); 7.60 (d, J=8.8, 1H).

b. Synthesis of Diaryl-substituted, Diphosphate Benzofuran Based Prodrugs

Figure 6:
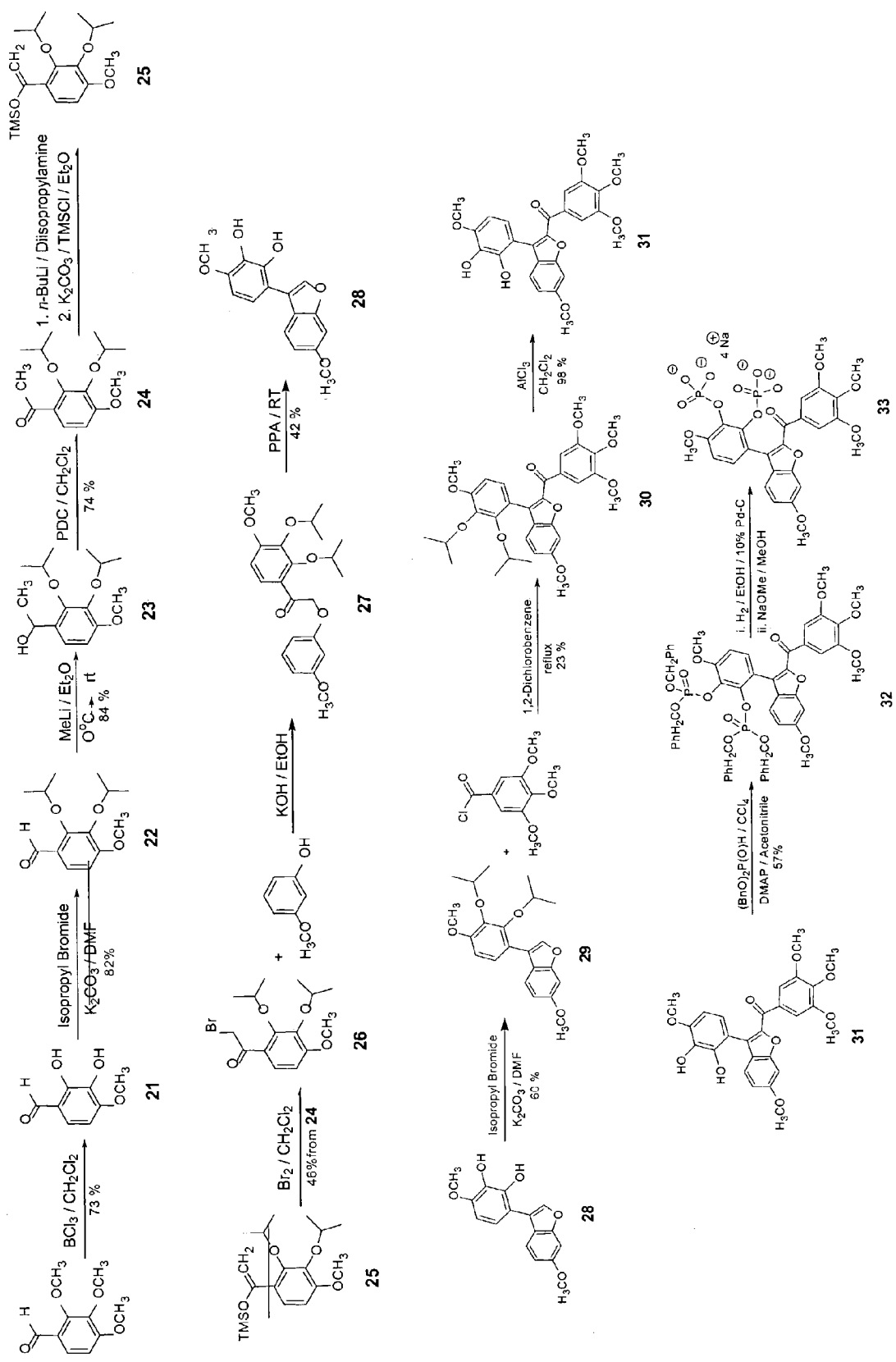
FIG. 6 illustrates the synthesis of an exemplary benzo[b]furan diphosphate prodrug construct.

It is now known that while CA4P is a potent vascular targeting and destruction agent in vivo, it is likely that CA1P (a diphosphate) may prove to be as active or even more active than CA4P in vivo. Since Ca4P is enzymatically converted to CA4, which in turn interacts with tubulin to cause vascular disruption, it is reasonable to expect that the new tubulin binding agents described herein may prove to be enhanced VTAs once functionalized as diphosphates. The syntheses of exemplary diphosphate benzofuran compound is illustrated in FIG. 6.

2, 3-dihydroxy-4-methoxybenzaldehyde 21

A dry CH$_2$Cl$_2$ (200 mL) solution of 2,3,4-trimethoxybenzaldehyde (19.6 g, 100 mmol), under nitrogen, was stirred for 10 min and BCl$_3$ (1.0M solution in CH$_2$Cl$_2$, 200 mL) was added. The reaction was stirred for 24 hours and a 10% sodium bicarbonate solution (40 g/360 mL) was added. The resulting solution was acidified with concentrated HCl to PH 1. The organic layer was separated, and the aq. layer was extracted with EtOAc (4×100 mL). The organic layer was dried with MgSO$_4$ and filtered through celite. After solvent evaporation, the crude mixture was recrystallized using (Hexanes/EtOAc:70/30) to afford 12.2 g (72.6 mmol, 73%) of a purple solid.

$^1$H-NMR (CDCl$_3$, 300 MHz): δ 3.98 (s, 3H); 5.58 (s, 1H); 6.62 (d, J=8.7, 1H); 7.14 (d, J=8.7, 1H); 9.75 (s, 1H); 11.12 (s, 1H).

2,3-diisopropoxy-4-methoxybenzaldehyde 22

To a solution of 21 (26.70 g, 158.7 mmol) in DMF (150 mL) under nitrogen, was added K$_2$CO$_3$ (65.84 g, 476.3 mmol) followed by 2-bromopropane (44.72 mL, 476.3 mmol) and heated to reflux (90° C.) for 12 hours. Water (200 mL) and EtOAc (200 mL) were added to the reaction mixture, the phases were separated, and the aqueous phase was extracted with EtOAc (3×200 mL). The combined organic solutions were dried over MgSO$_4$ and concentrated under reduced pressure. Purification by flash column chromatography (silica gel, elution with hexane) provided 32.85 g (1.30.2 mmol, 82%) of the diusopropyl-protected aldehyde 22 as a yellow oil.

$^1$H-NMR (CDCl$_3$, 300 MHz): δ 1.30 (d, J=6.1, 3H); 1.32 (d, J=6.1, 3H); 3.91 (s, 3H); 4.45 (septet, J=6.1, 1H); 4.82 (septet, J=6.1, 1H); 6.76 (d, J=8.8, 1H); 7.62 (d, J=8.8, 1H); 10.28 (s, 1H).

2,3-diisopropoxy-1-(1-hydroxyethyl)-4-methoxybenzene 23

To a solution of 22 (23.10 g, 91.56 mmol) in dry ethyl ether (150 mL) was added dropwise methyllithium (98.10 mL, 1.4 M in EtO$_2$, 1.37.3 mmol) at 0° C. under nitrogen. The reaction mixture was stirred for 2 h allowing too reach room temperature. The reaction was slowly quenched with water, the phases were separated, and the aqueous phase was extracted with ethyl ether (3×150 mL). The combined organic solutions were dried over MgSO$_4$ and concentrated over reduced pressure. Purification by flash column chromatography (silica gel, elution with hexanes/EtOAc: 80/20) provided the protected alcohol 20.62 g (76.77 mmol, 84%) as a pale yellow oil.

$^1$H-NMR (CDCl$_3$, 300 MHz): δ 1.26 (m, 12H); 1.48 (d, J=6.4, 3H); 3.82 (s, 3H); 4.38 (septet, J=6.1, 1H); 4.90 (septet, J=6.1, 1H); 5.14 (q, J=3.4, 1H); 6.65 (d, J=8.6, 1H); 7.04 (d, J=8.6, 1H).

2,3-diisopropoxy-4-methoxyacetophenone 24

To a solution of 23 (24.70 g, 92.05 mmol) in CH$_2$Cl$_2$ (150 mL) celite (4 g), and anhydrous K$_2$CO$_3$ (3.0 g) was added PDC (45.02 g, 119.6 mmol) in portions at 0° C. under nitrogen. The reaction mixture was stirred for 12 h allowing too reach room temperature. The reaction mixture was filtered through a short pad of celite/silica gel (50/50) rinsing well with CH$_2$Cl$_2$. The residue was concentrated onto silica gel under reduced pressure and subjected to flash column chromatography (silica gel, elution with hexanes/EtOAc: 90/10) to afford the diisopropyl-protected ketone 18.18 g (68.27 mmol, 74%) as a yellow solid.

$^1$H-NMR (CDCl$_3$, 300 MHz) δ 1.26 (d, J=6.2, 6H); 1.32 (d, J=6.2, 6H); 2.62 (s 3H); 3.89 (s, 3H); 4.47 (septet, J=6.2, 1H); 4.78 (septet, J=6.2, 1H) 6.70 (d, J=8.8, 1H); 7.63 (d, J=8.8, 1H).

1-(2,3-diisopropoxy-4-methoxyphenyl)-1-trimethylsilylethene 25

In a dry round bottom flask under nitrogen was placed dry ether (70 mL) and diisopropylamine (10.64 mL, 75.98 mmol), and the solution was cooled to 0° C. Butyllithium (30.42 mL of a 2.6M solution, 75.98 mmol) was added in a dropwise manner. Meanwhile, compound 24 (13.4 g, 50.3 mmol) was weighed into a 250 ml flask, put under argon, dissolved in dry ether (~70 mL), and the solution was added dropwise with good stirring to the cold LDA solution. After 5 min, chlorotrimethylsilane (9.64 mL, 75.9 mmol) was added dropwise, and the solution was allowed to stir for 12 hr. The reaction was then quenched with 10% NaHCO$_3$ (100 mL) followed by extraction with hexanes (3×200 mL), and dried over potassium carbonate. Filtration and concentration by rotary evaporation gave the crude TMS enol ether as a yellow oil.

$^1$H-NMR (CDCl$_3$, 300 MHz): δ 0.23 (s, 9H); 1.23 (d,J=6.2, 6H); 1.28 (d, J=6.2, 6H); 3.82 (s, 3H); 4.41 (septet, J=6.2, 1H); 4.55 (s, 1H); 4.68 (septet, J=6.2, 1H); 5.14 (s, 1H); 6.61 (d, J=8.8, 1H); 7.21 (d, J=8.8, 1H).

2,3-diisopropoxy-4-methoxy-2-bromoacetophenone 26

To a solution of the crude 25 (10.39 g, 30.72 mmol) in dry CH$_2$Cl$_2$ (35 mL) was added 1 g of powdered anhydrous K$_2$CO$_3$, and the mixture was cooled to 0° C. under nitrogen. Then bromide (1.42 mL, 27.6 mmol) was added slowly in a dropwise manner. After stilling a few minutes, the reaction was worked up by adding sodium thiosulfate solution, the phases separated, and the aqueous phase was extracted with CH$_2$Cl$_2$. The combined organic solutions were dried over MgSO$_4$ and the deep red oil was concentrated under reduced pressure. The crude mixture was dissolved in 80 mL of hexanes and placed in the refrigerator overnight. Isolation of the crystals provided 4.91 g (14.1 mmol, 46% from enol) of diisopropyl-protected bromide as red crystals.

$^1$H-NMR (CDCl$_3$, 300 MHz): δ 1.24 (d, J=6.2, 6H); 1.31 (s, J=6.2, 6H); 3.88 (s, 3H); 4.42 (septet, J=6.2, 1H); 4.63 (s, 1H); 4.85 (septet, J=6.2,1H); 6.72 (d, J=8.8, 1H); 7.48 (d, J=8.8, 1H). $^{13}$C-NMR (CDCl$_3$, 75 MHz): δ 22.34, 22.43, 36.98, 56.05, 75.64, 75.69, 107.04, 125.19, 126.00, 139.78, 151.71, 158.56, 192.72.

2,3-diisopropoxy-4-methoxy-alpha-[(3-methoxyphenyl) oxy]acetophenone 27

To a solution of KOH (1.35 g, 24.0 mmol) in ETOH (60.00 mL) and H$_2$O (30.00 mL) was added 3-methoxyphenol (1.71 mL, 15.5 mmol) at 0° C. After stirring for 10 min 26 (4.90 g, 14.1 mmol) in EtOAc (30.00 mL) was added in a dropwise fashion. The reaction mixture was stiffed for 12 h allowing too reach room temperature. The reaction mixture was quenched with water, the phases separated, and the aqueous phase extracted with EtOAc (3×100 mL). The combined organic solutions were dried over MgSO$_4$ and concentrated under reduced pressure.

3-(2',3'-hydroxy-4'-methoxyphenyl)-6-methoxybenzo[b]furan 28

To crude 27 (3.51 g,9.05 mmol), in a three neck round bottom flask, was added PPA (52.50 g) and stirred (mechanically) under nitrogen at room temperature for 2 hours. The reaction was quenched with ice water, the phases separated, and the aqueous layer was extracted with EtOAc (3×150 mL). The combined organic phases were dried over MgSO$_4$ and concentrated under reduced pressure. Purification by flash column chromatography (silica gel, elution with hexanes/EtOAc: 70/30) provided 1.11 g (12.9 mmol, 42%) of the diphenol as a white solid.

$^1$H-NMR (CDCl$_3$ 300 MHz): δ 3.87 (s, 3H); 3.93 (s, 3H); 5.50 (s, 1H); 5.62 (s, 1H); 6.59 (d, J=8.6, 1H); 6.91 (dd, J=2.2, 8.6, 1H); 7.07 (d, J=2.2, 1H); 7.11 (d, J=8.6, 1H) 7.62 (d, J=8.6, 1H) 7.86 (s, 1H). $^{13}$C-NMR (CDCl$_3$, 300 MHz): δ 55.71, 56.18, 96.00, 103.04, 111.77, 112.54, 116.68, 119.92, 120.33, 121.11, 132.75, 141.60, 142.19, 146.24, 156.23, 157.96.

3-(2',3'-diisopropoxy-4'-methoxyphenyl)-6-methoxybenzo[b]furan 29

To a solution of 28 (1.1 g, 3.8 mmol) in DMF (10 mL), under nitrogen, was added K$_2$CO$_3$ (1.60 mL, 11.5 mmol) followed by 2-bromopropane (1.08 mL, 11.5 mmol) and heated to reflux for 12 hours. Water (75 mL) and EtOAC (75 mL) were added to the reaction mixture, the phases separated, and the aqueous phase was extracted with EtOAc (3×30 mL). The combined organic solutions were dried over MgSO$_4$ and concentrated under reduced pressure. Purification by flash column chromatography (silica gel, elution with hexanes) afforded 0.84 g (2.2 mmol, 60%) of the diisopropyl-protected furan as a yellow oil.

$^1$H-NMR (CDCl$_3$, 300 MHz): δ 1.02 (d, J=6.2, 6H); 1.35 (d, J=6.2, 6H); 3.87 (s, 3H); 4.41 (septet, J=6.2, 1H); 4.53 (septet, J=6.2, 1H); 6.74 (d, J=8.6, 1H); 6.90 (dd, J=2.2, 8.7, 1H); 7.05 (d, J=2.2, 1H); 7.24 (d, J=8.6, 1H); 7.62 (d, J=8.7, 1H); 7.80 (s, 1H). $^{13}$C-NMR (CDCl$_3$, 75 MHz): δ 22.29, 22.61, 55.69, 55.90, 74.79, 75.36, 95.75, 106.93, 111.48, 118.35, 120.14, 120.58, 121.74, 123.77, 141.25, 142.02, 149.95, 153.77, 156.10, 157.78.

3-(2",3"-diisopropoxy-4"-methoxyphenyl)-6-methoxy-2-(3',4',5'-trimethoxybenzoyl) benzo[b]furan 30

To a solution of 29 (0.84 g, 2.2 mmol), in O-dichlorobenzene (15 mL), under nitrogen, was added 3, 4, 5-trimethoxybenzoylchloride (0.75 g, 3.4 mmol). The reaction mixture was heated to reflux (190° C.) and stirred for 36 hours. Solvent was removed by distillation under reduced pressure. After cooling to room temperature, a dark solid was formed which was dissolved in CH$_2$Cl$_2$. The reaction mixture was washed with saturated NaHCO$_3$, the phases separated, and the aqueous phase was extracted with CH$_2$Cl$_2$. The combined organic solutions were dried of MgSO$_4$ and concentrated under reduced pressure. Purification by flash column chromatography (elution with hexanes/EtOAc: 60/40) afforded 0.30 g (0.53 mmol, 23%) of the trimethoxybenzoyl furan as a white solid.

$^1$H-NMR (CDCl$_3$, 300 MHz): δ 0.60 (d, J=5.5, 3H); 0.97 (d, J=5.6, 3H); 1.06 (d, J=5.0, 3H); 3.70 (s, 3H); 3.74 (septet, J=6.2, 1H); 3.81 (s, 3H); 3.82 (s, 3H); 3.91 (s, 3H); 4.14 (septet, J=6.2, 1H); 6.75 (d, J=8.6, 1H); 6.97 (dd, J=2.2, 8.8, 1H); 7.00 (s, 2H); 7.15 (s, J=2.2, 1H) 7.27 (d, J=8.5, 1H) 7.56 (d, J=8.8, 1H). $^{13}$C-NMR (CDCl3, 75 MHz): δ 30.91, 55.79, 55.88, 55.98, 60.78, 95.71, 106.85, 107.21, 113.87, 120.16, 121.42, 122.44, 122.90, 123.88, 132.95, 141.46, 141.58, 146.93, 149.43, 152.32, 155.32, 156.32, 160.55, 185.41.

3-(2",3"-dihydroxy-4"-methoxyphenyl)-6-methoxy-2-(3',4',5'-trimethoxybenzoyl)benzo[b]furan 31

To a solution of 30 (0.30 g, 0.53 mmol) in CH$_2$Cl$_2$ (2 mL), under nitrogen, was added AlCl$_3$ (0.16 g, 1.2 mmol). The reaction mixture was stirred for 10 minutes allowing too reach room temperature. The reaction mixture was quenched with sat. ammonium chloride (5 mL), the phases separated, and the aqueous phase was extracted with CH$_2$Cl$_2$ (3×5 mL). The combined solutions were dried over MgSO$_4$ and concentrated under reduced pressure. Purification by flash column chromatography (silica gel, elution with hexanes/EtOAC: 60/40) afforded 0.25 g (0.52 mmol, 98%) of the desired diphenol as a yellow colored solid.

$^1$H-NMR (CDCl$_3$, 300 MHz): δ 3.90 (s, 6H); 3.92 (s, 3H); 3.95 (s, 6H); 5.94 (s, 1H) 6.66 (d, J=8.7, 1H); 6.92 (d, J=8.6, 1H); 6.99 (dd, J=2.2, 8.8, 1H); 7.06 (d, J=2.2, 1H); 7.34 (s, 2H); 7.55 (d, J=8.8, 1H) 8.21 (s, 1H). $^{13}$C-NMR (CDCl$_3$, 75 MHz): δ 56.28, 56.63, 56.70, 61.42, 95.49, 105.31, 108.53, 113.82, 114.98, 122.21, 122.41, 124.46, 128.08, 132.30, 136.55, 143.27, 143.54, 147.26, 148.36, 153.14, 156.70, 162.13, 186.42.

3-(3',4',5'-trimethoxybenzoyl)-2-(2",3"-tetrabenzyldiphosphate-4"-methoxyphenyl)-6-methoxybenzo[b]furan 32

To a solution of 31 (0.25 g, 0.52 mmol), under nitrogen, in acetonitrile (5 mL) was added CCl$_4$ (0.89 mL, 9.1 mmol)

at −25° C. After stirring for 10 min, ethyldiisopropylamine (0.38 mL, 2.1 mmol) and DMAP (0.10 g, 0.10 mmol) were added. Dibenzylphosphite (0.34 mL, 1.5 mmol) was added after 5 m,in and the mixture was stirred at −20° C. for 2 hrs. The reaction mixture was slowly warmed to room temperature and stirred for an additional 2 hrs at which point a KH$_2$PO$_4$ solution (5 mL, 0.5M) was added, the product was isolated by extraction with EtOAc (3×10 mL). The combined organic solutions were dried over MgSO$_4$ and concentrated under reduced pressure. Purification by flash column chromatography (silica gel, elution with hexanes/EtOAc: 50/50) yielded 0.20 g (0.20 mmol, 57%) of the desired dibenzyl phosphate as a colorless oil.

$^1$H-NMR (CDCl$_3$, 300 MHz): δ 3.69 (s, 6H); 3.84 (s, 3H); 3.87 (s, 3H); 3.90 (s, 3H); 4.5 (m, 2H) 4.67 (m, 2H) 5.21 (t, J=7.0, 4H) 6.89 (m, 6H); 6.99 (d, J=2.1, 1H); 7.26 (m, 20H); 7.46 (d, J=8.8, 1H). $^{13}$C-NMR (CDCl$_3$, 75 MHz): δ 55.75, 55.16, 56.23, 56.43, 60.38, 60.90, 69.57, 69.64, 69.82, 69.85, 95.37, 107.61, 109.45, 114.20, 118.22, 121.60, 123.25, 124.44, 127.55, 127.58, 127.87, 127.88, 128.17, 128.19, 128.25, 128.35, 128.40, 128.43, 132.54, 135.34, 135.42, 135.44, 135.51, 135.93, 136.00, 136.04, 136.11, 142.16, 148.01, 152.72, 155.64, 160.96, 183.17, $^{31}$P (CDCl$_3$, 120 MHz): δ 5.83 (d, J=6.6), 6.30 (d, J=6.8).

Oxi-com 223, 3-(3',4',5'-trimethoxybenzoyl)-2-(3'-disodiumphosphate-4'-methoxyphenyl)-6-methoxybenzo[b]furan 33

To a solution of 32 (0.20 g) in 100% ethanol (3 mL), under argon, was added 10% palladium-carbon (0.10 g). The flask was then closed and all air was evacuated by vacuum pump. A balloon filled with Hydrogen (H$_2$), a stopcock valve, and a needle was used to add hydrogen to the flask. The flask was then evacuated again and hydrogen gas was passed into the flask again using the hydrogen filled balloon. The reaction proceeded for 2 hrs then checked by reverse phase thin layer chromatography (TLC). The reaction mixture was filtered through a pipet filled with celite and concentrated under reduced pressure to give a greenish yellow foam. To a solution of the crude phosphate 33, (0.10 g, 0.16 mmol) in dry methanol (5 mL), in a pear-shaped flask, was added sodium methoxide (0.15 mL of a 4.37M solution, 0.65 mmol) and the reaction mixture was kept in the refrigerator. The product was isolated using several reverse phase TLC plates.

$^1$H-NMR (CDCl$_3$, 300 MHz): δ 3.51 (s, 3H); 3.53 (s, 6H); 3.62 (s, 3H); 3.72 (s, 3H); 6.35 (s, 2H); 6.69 (m, 2H); 6.79 (d, J=8.9, 1H); 6.82 (d, J=1.9, 1H); 7.14 (d, J=8.3, 1H). $^{31}$P(CDCl$_3$, 120 MHz): δ−1.91, 3.79.

Example 4

Synthesis of Aryl-substituted Indenes and Corresponding Prodrugs

Figure 7:
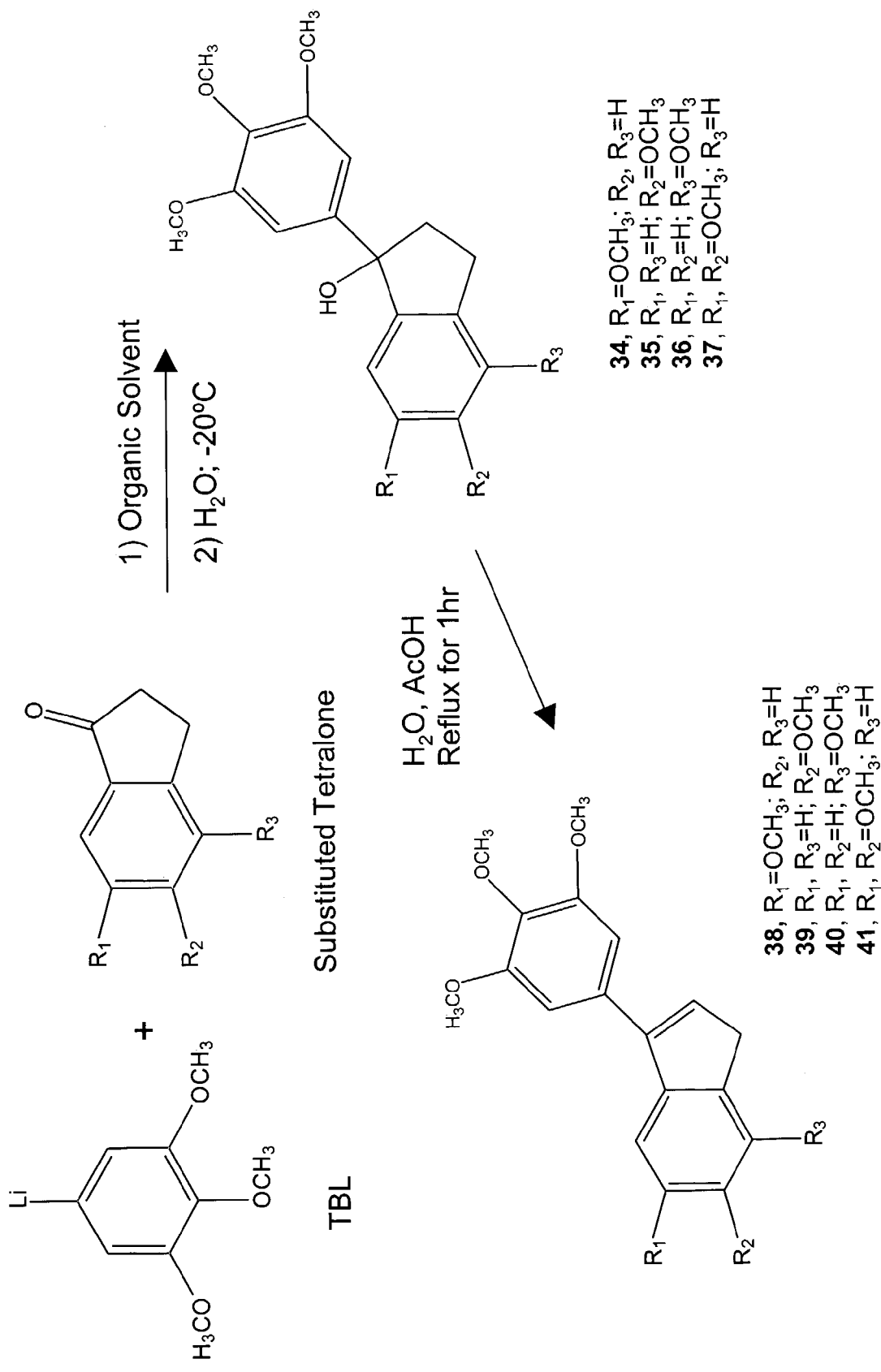
FIG. 7 illustrates a generalized procedure for the synthesis of indene analogs.

Our interest in preparing the following aryl-substituted Indene ligands was based on our molecular recognition studies which suggest an optimal aryl-aryl distance (centroid to centroid) for enhanced tubulin binding. Exemplary aryl-substituted Indene ligands were synthesized according to the generalized synthetic scheme illustrated in FIG. 7.

a. Synthesis of Aryl-substituted Tetrahydronaphthalen-1-ol

To a stirred solution of n-butyllithium (3.7 mL, 1.6 M in hexane solution,6.0 mol) in dry ether (40 mL), a solution of 3,4,5-trimethoxyphenylbromide (0.74 g, 3.0 mol) in ether (20 mL) was added under dry nitrogen at −78° C. The solution was stirred for 1 h in order to form 3,4,5-trimethoxyphenyllithium ("TPL"). Substituted tetralone reagent (3.0 mol) was added at −20° C., and the stirring was continued for 2 h (−20° C.-RT). The mixture was partitioned between CH$_2$Cl$_2$ and water, the organic layer was dried over anhydrous sodium sulfate, and, after filtration, the organic layer was concentrated in vacuo to provide a tetrahydronaphthalen-1-ol as a yellow oil. Each compound was purified by column chromatography.

34. (56% yield) $^1$H-NMR (CDCl$_3$, 300 MHz) δ 2.19 (s, 1H), 2.48 (m, 2H), 2.91 (m, 1H), 3.10 (m, 1H), 3.76 (s, 3H), 3.82 (s, 6H), 3.86 (s, 3H), 6.64 (s, 2H), 6.67 (d, J=2.4 Hz, 1H), 6.91 (dd, J=2.4, 6.5 Hz, 1H), 7.27 (d, J=6.5 Hz, 1H). $^{13}$C-NMR (CDCl$_3$, 75 MHz) δ 29.0, 45.4, 55.5, 56.1, 60.8, 85.7, 102.9, 108.4, 115.4, 125.7, 135.9, 136.6, 141.9, 148.9, 152.8, 159.2. HRMS (EI) M$^+$, calcd for C$_{19}$H$_{22}$O$_5$ 330.1467, found 330.1466.

35. (54% yield) $^1$H-NMR (CDCl$_3$, 300 MHz) δ 2.12 (s, 1H), 2.48 (t, J=6.2 Hz, 2H), 2.90 (m, 1H), 3.15 (m, 1H), 3.81 (s, 6H), 3.84 (s, 3H), 3.86 (s, 3H), 6.65 (s, 2H), 6.78 (dd, J=2.3, 8.4 Hz, 1H), 6.86 (d, J=2.3 Hz, 1H), 7.04 (d, J=8.4 Hz, 1H). $^{13}$C-NMR (CDCl$_3$, 75 MHz) δ 30.0, 45.7, 56.0, 56.4, 61.2, 85.6, 103.4, 110.2, 113.7, 125.2, 137.0, 140.4, 142.8, 145.5, 153.2, 160.7. HRMS (EI) M$^+$, calcd for C$_{19}$H$_{22}$O$_5$ 330.1467, found 330.1470.

36. (50% yield) $^1$H-NMR (CDCl$_3$, 300 MHz) δ 2.18 (s, 1H), 2.50 (m, 2H), 2.95 (m, 1H), 3.07 (m, 1H), 3.80 (s, 6H), 3.85 (s, 3H), 3.89 (s, 3H), 6.64 (s, 2H), 6.75 (d, J=7.6 Hz, 1H), 6.82 (d, J=7.4 Hz, 1H), 7.22 (d, J=8.0 Hz, 1H). $^{13}$C-NMR (CDCl$_3$, 75 MHz) δ 26.6, 44.5, 55.3, 56.1, 60.8, 86.1, 103.0, 109.8, 116.0, 128.7, 131.9, 136.6, 142.1, 149.4, 152.8, 156.0. HRMS (EI) M$^+$, calcd for C$_{19}$H$_{22}$O$_5$ 330.1467, found 330.1466.

37. (45% yield) $^1$H-NMR (CDCl$_3$, 300 MHz) δ 2.11 (s, 1H), 2.49 (m, 2H), 2.90 (m, 1H), 3.09 (m, 1H), 3.79 (s, 3H), 3.80 (s, 6H), 3.86 (s, 3H), 3.92 (s, 3H), 6.62 (s, 2H), 6.65 (s, 1H), 6.85 (s, 1H). $^{13}$C-NMR (CDCl$_3$, 75 MHz) δ 30.1, 45.9, 56.4, 56.5, 61.2, 86.5, 103.3, 106.8, 107.8, 136.5, 137.0, 139.5, 142.8, 149.0, 150.2, 153.2. HRMS (EI) M$^+$, calcd for C$_{20}$H$_{24}$O$_6$ 360.1573, found 360.1564.

b. Synthesis of Aryl-substituted Dihydronaphthalenes. To a solution of acetic acid (10 mL) in H$_2$O (60 mL), compounds 34,35,36,37, (1 mol) were added respectively. The solution was heated to reflux for 1 hour, and then cooled down to RT. NaHCO$_3$ (20 mL, saturated solution) was added, and the mixture was partitioned between CH$_2$Cl$_2$ and water. The organic layer was dried over anhydrous sodium sulfate, after filtration, the organic layer was concentrated in vacuo to provide the following compounds as a yellow oil. Each compound was purified by column chromatography.

38. (91% yield) $^1$H-NMR (CDCl$_3$, 300 MHz) δ 3.45 (d, J=1.3 Hz, 2H), 3.83 (s, 3H), 3.91 (s, 9H), 6.58 (t, J=1.9 Hz, 1H), 6.80 (s, 2H), 6.83 (dd, J=2.3, 8.2 Hz, 1H), 7.14 (d, J=2.3 Hz, 1H), 7.42 (d, J=8.2 Hz, 1H). $^{13}$C-NMR (CDCl$_3$, 75 MHz) δ 37.4, 55.5, 56.1, 60.9, 104.6, 106.1, 110.8, 124.5, 131.7, 132.1, 136.7, 137.5, 145.0, 145.2, 153.3, 158.8. HRMS (EI) M$^+$, calcd for C$_{19}$H$_{20}$O$_4$ 312.1362, found 312.1361. Anal. Calcd for C$_{19}$H$_{20}$O$_4$: C, 73.06; H, 6.45. Found: C, 73.21; H, 6.44.

39. (90% yield) $^1$H-NMR (CDCl$_3$, 300 MHz) δ 3.48 (s, 2H), 3.86 (s, 3H), 3.91 (s, 9H), 6.42 (s, 1H), 6.89 (s, 2H), 6.91 (dd, J=2.7, 7.8 Hz, 1H), 7.13 (d, J=2.7 Hz, 1H), 7.49 (d, J=8.0 Hz, 1H). $^{13}$C-NMR (CDCl$_3$, 75 MHz) δ 38.0, 55.6, 56.1, 60.9, 104.6, 110.6, 111.8, 12.5, 128.4, 132.0, 136.9, 137.5, 144.7, 146.6, 153.3, 158.0. HRMS (EI) M$^+$, calcd for C$_{19}$H$_{20}$O$_4$ 312.1362, found 312.1357. Anal. Calcd for C$_{19}$H$_{20}$O$_4$: C, 73.06; H, 6.45. Found: C, 72.98; H, 6.52.

40. (90% yield) $^1$H-NMR (CDCl$_3$, 300 MHz) δ 3.47 (d, J=1.9 Hz, 2H), 3.91 (s, 9H), 3.94 (s, 3H), 6.57 (t, J=1.9 Hz, 1H), 6.81 (s, 2H), 6.83 (d, J=8.2 Hz, 1H), 7.24 (d, J=7.6 Hz, 1H), 7.33 (d, J=7.7 Hz, 1H). $^{13}$C-NMR (CDCl$_3$, 75 MHz) δ 35.0, 54.9, 55.7, 60.5, 104.3, 107.0, 113.0, 127.5, 130.4, 131.2, 131.4, 137.0, 144.6, 145.2, 152.8, 155.1. HRMS (EI) M$^+$, calcd for C$_{19}$H$_{20}$O$_4$ 312.1362, found 312.1361. Anal. Calcd for C$_{19}$H$_{20}$O$_4$: C, 73.06; H, 6.45. Found: C, 73.12; H, 6.55.

41. (84% yield) $^1$H-NMR (CDCl$_3$, 300 MHz) δ 3.46 (d, J=1.8 Hz, 2H), 3.88 (s, 3H), 3.92 (s, 9H), 3.94 (s, 3H), 6.45 (t, J=1.9 Hz, 1H), 6.80 (s, 2H), 7.13 (s, 1H), 7.14 (s, 1H), $^{13}$C-NMR (CDCl$_3$, 75 MHz) δ 38.0, 56.1, 56.2, 61.0, 103.8, 104.5, 108.2, 129.2, 132.0, 136.5, 137.2, 137.5, 144.9, 147.4, 148.0, 153.4. HRMS (EI) M$^+$, calcd for C$_{20}$H$_{22}$O$_5$ 342.1467, found 342.1464.

Example 5

Synthesis of an Enediyne Based Prodrug

Figure 8:
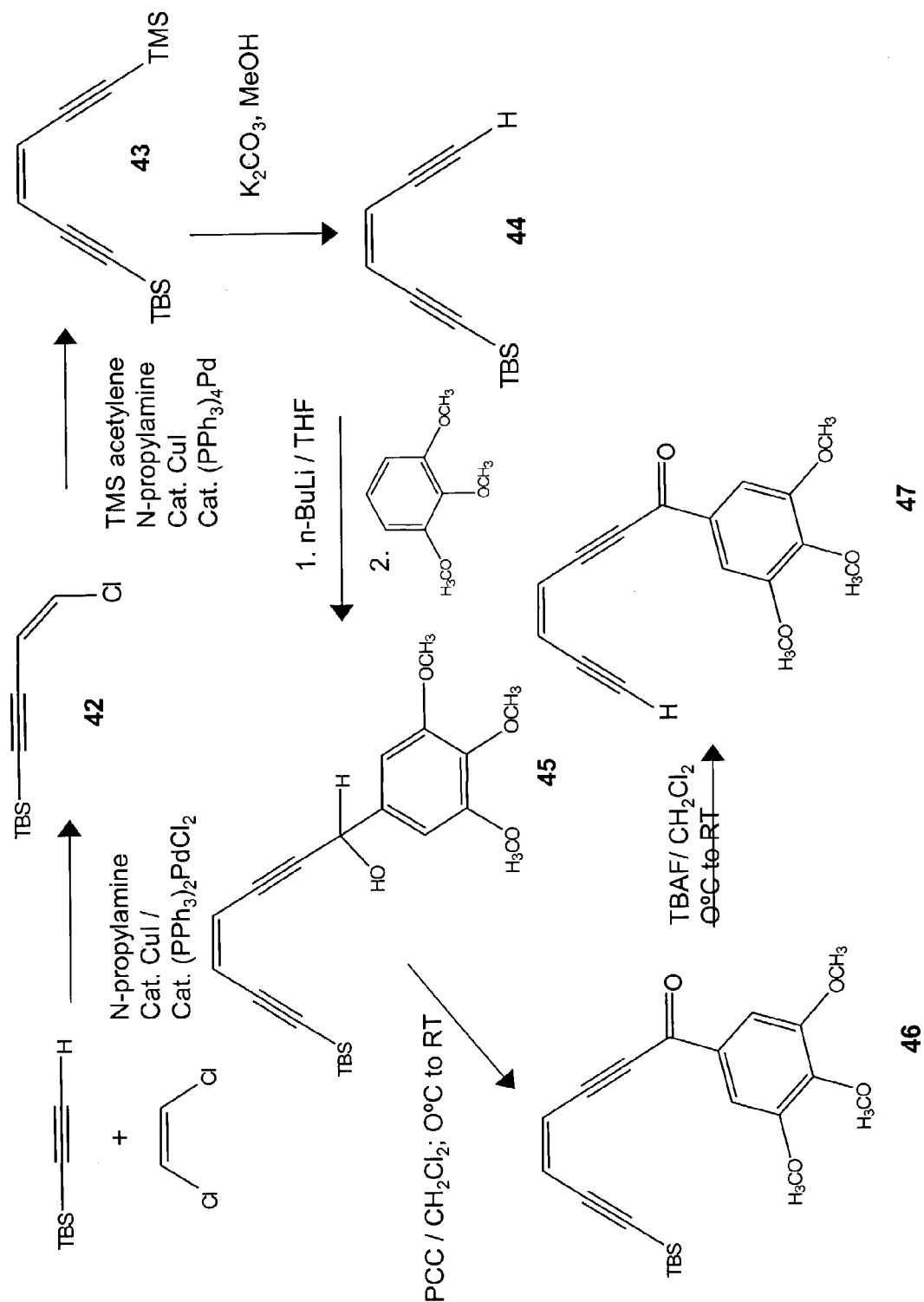
FIG. 8 illustrates the synthesis of an exemplary enediyne ligand.

We have recently prepared an enediyne based compound 47 (see FIG. 8) in which one aryl ring mimics the trimethoxy aryl ring of CA4, while a triple bond moiety functions as a pi bond rich mimic of the second aryl ring of CA4. Since this compound demonstrates strong cytotoxicity and excellent inhibition of tubulin polymerization, a natural extension is the preparation of phosphate and phosphoramidate prodrugs following the synthetic protocols established in this application. A further extension of this work will be the preparation of analogous enediyne prodrug constructs which do not contain the carbonyl group at either terminus of the enediyne bridge (diaryl enediyne constructs) and compounds which contain a carbonyl group at both termini of the enediyne bridge connecting the bridge to an appropriately substituted aryl ring.

Andrew Myers and co-workers along with several other groups have reported the synthesis of cis-enediynes that are utilized for the total synthesis of dynemicin and calicheamicin (Myers et al, J. Am. Chem. Soc., 1997, 119: 6072–6094). We have utilized a similar synthetic route to prepare modifed cis-enediynes as tubulin binding ligands. The cis-enediynes are prepared by coupling TBS-acetylene to cis-1,2-dichloroethylene in the presence of dichloro-bis-triphenylphosphine palladium (II) catalyst, CuI, and n-propylamine to yield eneyne 42. A second coupling reaction of eneyne 42 with TMS-acetylene and n-propylamine, an acid quenching base, in the presence of the catalysts tetrakis-triphenylphosphine palladium and CuI catalysts, resulted in enediyne 43 which is protected on both ends by TBS and TMS groups which can be preferentially deprotected. Deprotection of the TMS group with K$_2$CO$_3$ in methanol afforded compound 44 which upon lithiation with n-BuLi in THF followed by reaction with 3,4,5-trimethoxybenzaldehyde resulted in the formation of the alcohol.

To a well-stirred, cooled (−78° C. dry ice/acetone) solution of tert-butyl[(Z)-3-hexene-1,5-diynyl] dimethylsilane (0.546 g, 2.87 mmol) in THF (20 mL) was lithiated by adding n-BuLi (2.5 M sol. in THF, 1.15 mL, 2.875 mmol). After stirring at −10° C. for 40 min, the temperature was returned to −78° C. and 3,4,5-trimethoxy-benzaldehyde (1.520 g, 6.590 mmol) in THF (5 mL) was added. After 12 h (−78° C. to r.t.) the reaction mixture was quenched with water and the product was isolated by extraction with EtOAC, followed by washing with brine and drying over Na$_2$SO$_4$. Removal of the solvent followed by purification by flash chromatography (80:20 hexanes:EtOAc) afforded the desired alcohol 1-[(3',4',5'-trimethoxyphenyl)-carbinol]-6-(tert-butyl-dimethylsilyl)-(Z)-3-ene-1,5-hexadiyne, 45 as a yellow colored solid.

45. (0.697 g, 1.80 mmol, 63%) $^1$H-NMR (CDCl$_3$, 360 MHz) δ 6.79 (s, 2H, ArH), 5.91 (ABq, J=11.0 Hz, 10.9 Hz, 2H), 5.78 (s, br, —OH), 0.93 (s, 9H, —CH$_3$), 0.11 (d, J=2.3 Hz, 6H, —CH$_3$). HRMS (EI) M$^+$ calcd for C$_{22}$H$_{30}$O$_4$Si 386.1913, found 386.1913. Anal. calcd for C$_{22}$H$_{30}$O$_4$Si: C, 68.36; H, 7.82. Found: C, 68.36; H, 7.92.

Oxidation of alcohol 45 was accomplished in CH$_2$Cl$_2$(30 mL) at 0° C. with the addition of PCC (0.712 g, 3.30 mmol). The reaction mixture was stirred at room temperature for 3 h and then quenched with water and subjected to a standard work-up (EtOAc, brine, and drying over Na$_2$SO$_4$). Solvent removal followed by purification by column chromatography (initially 90:10 hexanes: EtOAc increasing polarity of the solvent to 80:20 hexanes:EtOAc) gave the desired 1-(3,4,5-trimethoxybenzoyl)-6-(tert-butyldimethylsilyl)-(Z)-3-ene-1,5-hexadiyne, 46, as a yellow colored oil.

46. (0.370 g, 0.962 mmol, 53%) $^1$H-NMR (CDCl$_3$, 300 MHz) δ 7.44 (s, 2H, ArH), 6.13 (ABq, J=11.08 Hz, 10.98 Hz, 2H, —CH═CH—), 3.95 (s, 3H, —OCH$_3$), 3.94 (s, 3H, —OCH$_3$), 0.90 (s, 9H, —C(CH$_3$)$_3$), 0.11 (s, 6H, —Si(CH$_3$)$_2$). $^{13}$C-NMR (CDCl$_3$, 90 MHz) δ 176.3, 153.0, 143.5, 132.0, 124.8, 117.6, 107.0, 105.3, 101.7, 92.7, 89.3, 60.9, 56.2, 25.9, 16.4, −5.0.

Deprotection of the TBS group on 46 was accomplished in CH$_2$Cl$_2$ (10 mL) at 0° C. under nitrogen, by addition of TBAF (1M in THF, 0.300 ml, 0.300 mmol). After stirring for 12 h, the reaction was quenched with water and subjected to a standard work-up protocol (CH$_2$Cl$_2$, brine, and drying over sodium sulfate). Solvent was removed under reduced pressure and the product was purified by column chromatography (90:10 hexanes:ethyl acetate) to afford the enediyne 1-(3,4,5-trimethoxybenzoyl)-(Z)-3-ene-1,5-hexadiyne 47 as an off-white solid which turned brownish in color on standing for several minutes.

47. (0.027 g, 0.101 mmol, 56%) $^1$H-NMR (CDCl$_3$, 300 MHz) δ 7.49 (s, 2H, ArH), 6.19 (ABq, J=11.12 Hz, 11.05 Hz, 2H, —CH═CH—), 3.95 (s, 3H, —OCH$_3$), 3.94 (s, 3H, —OCH$_3$), 3.57 (d, J=1.72 Hz, 1H, —CH). $^{13}$C-NMR (CDCl$_3$, 90 MHz) δ 176.4, 153.0, 143.7, 131.8, 124.0, 119.2, 107.1, 92.7, 88.2, 87.7, 80.3, 60.9, 56.3. HRMS (EI) M$^+$ calcd for C$_{16}$H$_{14}$O$_4$ 270.0892, found 270.0889. Anal. calcd for C$_{16}$H$_{14}$O$_4$: C, 71.10; H, 5.22. Found: C, 71.20; H, 5.28.

Example 6

Inhibition of Tubulin Polymerization Assay

IC$_{50}$ values for tubulin polymerization were determined according to a previously described procedure (Bai et al, Cancer Research, 1996). Purified tubulin is obtained from bovine brain cells as described in Hamel and Lin (Hamel and Lin, Biochemistry, 1984). Various amounts of inhibitor were preincubated for 15 minutes at 37° C. with purified tubulin. After the incubation period, the reaction was cooled and GTP was added to induce tubulin polymerization. Polymerization was then monitored in a Gilford spectrophotometer at 350 nm. The final reaction mixtures (0.25 ml) contained 1.5 mg/ml tubulin, 0.6 mg/ml microtubule-associated proteins (MAPs), 0.5 mM GTP, 0.5 mM MgCl$_2$, 4% DMSO and 0.1M 4-morpholineethanesulfonate buffer (MES, pH 6.4). IC$_{50}$ is the amount of inhibitor needed to inhibit tubulin polymerization 50% with respect to the amount of inhibition that occurs in the absence of inhibitor. The results are listed in Table 1 below.

TABLE 1

In Vitro Inhibition of Tubulin Polymerization.

| Compound | IC$_{50}$ (µM) |
|---|---|
| CA-4 | 1.2 (±0.02) |
| Oxi-com 139, 7 | 0.5–0.75 |
| Oxi-com 140, 8 | 1–4 |
| Oxi-com 194, 17 | 1.0–4.0 |
| Oxi-com 195, 19 | 4–10 |
| 28 | 1–4 |
| 31 | 1–4 |
| Indane, 35 | 10–40 |
| Indene, 39 | 4–10 |
| Enediyne, 47 | 2–4 |

Example 7

In vitro Cytotoxicity Activity Against Cancer Cell Lines a) Human Cancer Cell Lines The activity of several compounds were tested against a variety of cell lines derived from human tumors, using an assay system similar to a procedure previously described (Monks et al, J. Natl. Cancer Inst., 1991). Briefly, the cell suspensions, diluted according to the particular cell type and the expected target cell density (5,000–40,000 cells per well based on cell growth characteristics), were added by pipet (100 µl) to 96-well microtiter plates. Inoculates were allowed a preincubation time of 24–28 hours at 37° C. for stabilization. Incubation with the inhibitor compounds lasted for 48 hours in 5% CO$_2$ atmosphere and 100% humidity. Determination of cell growth was performed by in situ fixation of cells, followed by staining with a protein-binding dye sulforhodamine B (SRB), which binds to the basic amino acids of cellular macromolecules. The solubilized stain was measured spectrophotometrically.

Compounds were evaluated in terms of growth inhibitory activity against several human cancer cell lines including: central nervous system ("CNS", SF-295 or SF-268), pancreas (BXPC-3), non-small cell lung cancer ("lung-NSC", NCI-H460), breast (MCF-7), colon (KM20L2), ovarian (OVCAR-3), pharyngeal (FADU), or prostate (DU-145). The results are described in Table 2 below. The growth inhibition GI$_{50}$ (defined as the dosage required to inhibit tumor cell growth by 50%) is listed for each cell line.

b) Murine Cancer Cell Lines

The following compounds were tested for in vitro antiproliferative activity against the murine hemangioendothelioma MHEC-5T cell line using a standard MTT assay (see Mosman, J. Immunol. Methods, 1983). In actively proliferating cells, an increase in MTT conversion is spectrophotometrically quantified by the reduction of MTT (3-[4,5-dimethylthiazol-2-yl]-2,5-diphenyl tetrazolium bromide) to the insoluble formazan dye by enzymes associated with metabolic activity. A compound with growth inhibitory activity will cause a reduction in dye formation relative to cells exposed to a vehicle control. The IC$_{50}$ value (defined as the amount of compound required to inhibit growth of 50% of cells with respect to a control treatment) for each compound was determined at one hour and five days at (see Table 3 below).

TABLE 3

In vitro Cytotoxicity against Murine cancer cell lines

| Compound | IC$_{50}$ (µM) at 1 hour | IC$_{50}$ (µM) at 5 days |
|---|---|---|
| CA4P | 0.8 | 0.002 |
| Oxi-com 140, 8 | >11.2 | 0.129 |
| Oxi-com 194, 17 | >25 | 0.1 |
| Oxi-com 195, 19 | >25 | 0.1 |
| Oxi-com 223, 33 | >50 | >1.4 |

Example 8

Inhibition of Tumor Blood Flow

The antivascular effects of the diphosphate BbF, Oxi-com 223, was assessed in tumor-bearing mice using a Fluorescent Bead Assay. A MHEC-5T hemangioendothelioma tumor model was established by subcutaneous injection of 0.5×10$^6$ cultured transformed cell murine myocardial vascular endothelial cell line ("MHEC5-T") cells into the right flank of Fox Chase CB-17 Severe Combined Immunodeficient ("SCID") mice. When transplanted tumors reached a size of 500 mm$^3$ (a size without development of necrosis), the mice received a single intraperitoneal (i.p.) injection of saline control or compound at doses ranging from 3.2 to 25 mg/kg. At 24 hours post-treatment, mice were injected intravenously with 0.25 ml of diluted FluoSphere beads (1:6 in physiological saline) in the tail vein, sacrificed after 3 minutes, and tumor

TABLE 2

In vitro Cytotoxicity against Human Cancer Cell Lines

GI$_{50}$ (µg/ml) for Cell Line

| Compound | SF-295 (*SF.268) | BXPC-3 | NCI-H460 | MCF-7 | KM20L2 | DU-145 | OVCAR-3 | FADU |
|---|---|---|---|---|---|---|---|---|
| Oxi-com 139, 7 | 0.032 | 0.32 | 0.0261 | 0.035 | 0.28 | 0.034 | — | — |
| Oxi-com 140, 8 | 0.11 | 0.35 | 0.035 | 0.028 | 0.22 | 0.045 | — | — |
| Oxi-com 194, 17 | *0.057 | 0.75 | 0.037 | 0.042 | 3.9 | 0.047 | — | — |
| Oxi-com 195, 19 | *0.062 | 2.3 | 0.05 | 0.042 | 3.8 | 0.05 | — | — |
| Indane, 35 | *1.3 | 0.54 | 0.32 | 0.44 | 0.84 | 2.9 | — | — |
| Indene, 39 | *1.7 | 0.44 | 0.97 | 0.44 | 1.3 | 2.5 | — | — |
| Enediyne, 47 | 1.7 | 1.4 | 1.7 | — | — | 0.54 | 0.53 | 0.95 | was excised for cryosectioning. Tumor cryosections at a thickness of 8 μm were directly examined using quantitative fluorescent microscopy. Blood vessels were indicated by blue fluorescence from injected beads. For quanitification, image analysis of 3 sections from three tumors treated in each group were examined and vascular shutdown was expressed as vessel area (mm$^2$) per tumor tissue area (mm$^2$) as a percentage of the control ("% VAPM"). Compounds of the present invention were tested for antivascular effects at two dosages (100 mg/kg and 10 mg/kg) using the same Fluorescent Bead Assay as in the previous experiment. The results are summarized in Table 5 below.

TABLE 5

Vascular Targeting Activity

| Compound | % VAPM at 100 mg/kg dose | % VAPM at 10 mg/kg dose |
|---|---|---|
| Oxi-com 223, 33 | 51 | 10 |

Example 9

Evaluation of Tumor Growth Control in vivo

The antitumor activity of BbT prodrug 8 was assessed in female tumor-bearing mice by measuring its effects on tumor volume in comparison with CA4P. A human breast cancer MDA-MB-231 model was established by subcutaneous injection of cultured MDA-MB-231 cells (1×10$^6$) in Fox Chase CB-17 SCID mice.

Figure 9A:
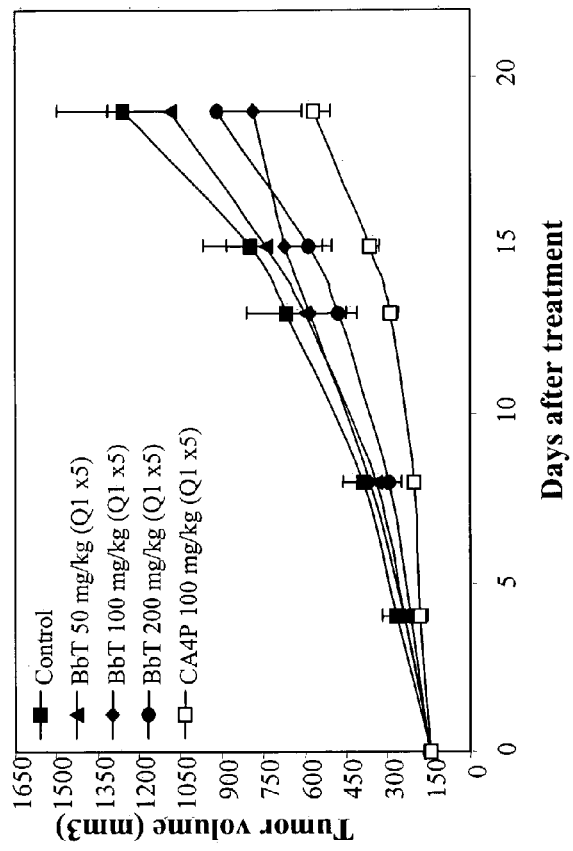
FIG. 9A depicts in vivo biological data for BbT Prodrug 8 in an animal model xenografted with the human breast cancer MDA-MB-231.
Figure 9B:
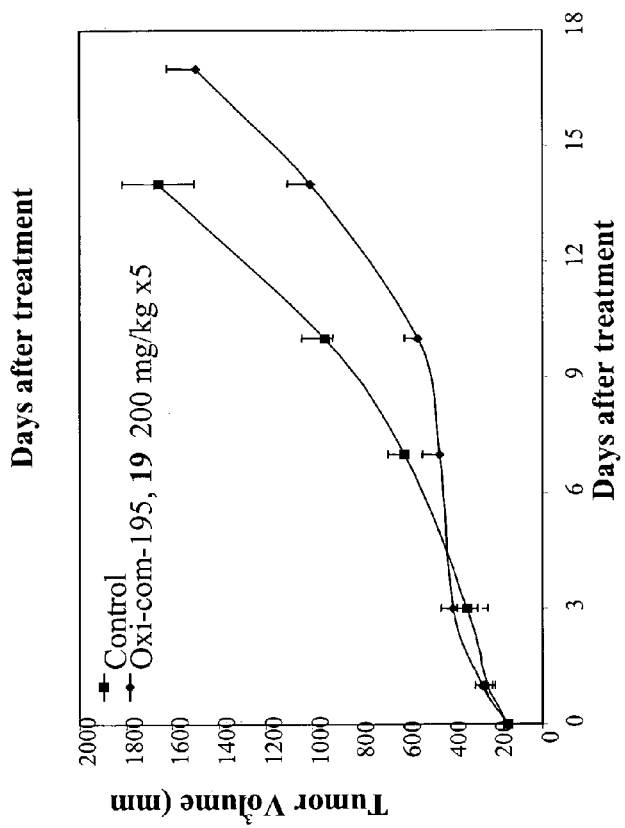
FIG. 9B depicts in vivo biological data for BbF Prodrug 19 in the same model.

Mice were administered CA4P or BbT prodrug in saline carrier at 400 mg/kg by intraperitoneal (i.p.) injection after 1 week of MDA-MB inoculation. Saline carrier only was used as the control treatment. On Days 1, 2 and 6 post-treatment, tumors were measured by width and length by a caliber. Tumor volume was calculated according to the following formula: Length×Width$^2$×0.4. The relative anti-tumor effects are illustrated in FIG. 9. Administration of either drug significantly inhibited tumor growth relative to control treatment.

Other Embodiments

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. For instance, in addition to the various metal salts described for the phosphates and phosphoramidates, any appropriate metal or non-metal cation and, in fact, any appropriately related salt construct can be employed without departing from the spirit and scope of the invention. For therapeutic and/or prophylactic anti-tumor purposes, the prodrugs of the present invention would be administered at a dosage of from about 5 mg/m$^2$ to about 100 mg/m$^2$ while intravascular infusion of the prodrug is preferred other modes of parenteral topical or enteral administration are usable under certain conditions.

The present invention also involves uses of the novel compounds described in manners relating to their useful effects on tubulin polymerization and abnormal vasculature. Certainly a method for inhibiting tubulin polymerization is a part of the present invention. This involves contacting a tubulin containing system with an effective amount of a compound described in the present invention. This tubulin containing system may be in a tumor cell, thereby inhibiting neoplastic disease by administering an effective amount of a compound of the present invention. Patients may thus be treated. In cases of cancer treatment, it is believed that many neoplasias such as leukemia, lung cancer, colon cancer, thyroid cancer, CNS, melanoma, ovarian cancer, renal cancer, prostate cancer and breast cancers may be effectively treated by the administration of an effective amounts of the compounds described in the present invention. Pharmaceutical preparations may be prepared by mixing the compounds of the present invention with a pharmaceutically acceptable carrier. This may be in tablet or intravascular form. In one important aspect, macular degeneration, and related diseases of the eye where vascularization is involved, may be treated by a method comprising administering an effective amount of a compound described in the present invention. Psoriasis may also be treated by administering an effective amount of the compound of the present invention. Likewise, any disease or condition caused or enhanced by undesired vascularization may be treated by administering an effective amount of a compound of the present invention.

In addition to their tumor-selective vascular targeting and destruction capabilities, it is contemplated that all the compounds of the present invention have potential application in the treatment of other diseases where the issue of vascularization is of great significance. Representative examples of these diseases include: diseases associated with ocular neovascularization (corneal and retinal), psoriasis and arthritis. All such similar substitutes and modifications apparent to those skilled in the art are deemed to be within the spirit, scope and concept of the invention as defined by the appended claims.

REFERENCES

The following citations are incorporated in pertinent part by reference herein for the reasons cited.

1. Bai, R.; Schwartz, R. E.; Kepler, J. A.; Pettit, G. R.; Hamel, E., Characterization of the Interaction of Cryptophycin with Tubulin: Binding in the Vinca Domain, Competitive Inhibition of Dolastatin 10 Binding, and an Unusual Aggregation Reaction, *Cancer Res.*, 1996,56,4398–4406.

2. Boger, D. L.; Curran, T. T., Synthesis of the Lower Subunit of Rhizoxin, *J. Org. Chem.* 1992, 57, 2235.

3. Chaplin D J, Pettit G R, Hill S A. Anti-vascular approaches to solid tumor therapy: Evaluation of combretastatin A4 phophate. Anticancer Res., 1999; 19:189–196.

4. Chavan, A. J.; Richardson, S. K.; Kim, H.; Haley, B. E.; Watt, D. S., Forskolin Photoaffinity Probes for the Evaluation of Tubulin Binding Sites, *Bioconjugate Chem.* 1993, 4,268.

5. Chen, Z.; Mocharla, V. P.; Farmer, J. M.; Pettit, G. R.; Hamel, E.; Pinney, K. G. Preparation of New Anti-Tubulin Ligands through a Dual-Mode, Addition-Elimination Reaction to a Bromo-Substituted α,β-Unsaturated Sulfoxide. *J. Org. Chem.*, 2000, 65, 8811–8815.

6. Cortese, F.; Bhattacharyya, B.; Wolff, J., Podophyllotoxin as a Probe for the Colehicine Binding Site of Tubulin, *J. Biol. Chem.*, 1977, 252, 1134.

7. Cushman, M.; Nagarathnam, D.; Gopal, D.; Chakraborti, A. K.; Lin, C. M.; Hamel, E. Synthesis and Evaluation of Stilbene and Dihydrostilbene Derivatives as Potential Anticancer Agents That Inhibit Tubulin Polymerization, *J. Med. Chem.* 1991, 34, 2579.

8. Dark, G. G., Hill, S. A., Prise, V. G., Tozer, G. M., Pettit, G. R., Chaplin, D. J., Combretastatin A-4, an Agent That Displays Potent and Selective Toxicity Toward Tumor Vasculature, *Cancer Res.*, 1997, 57, 1829–1834.

9. Davis P D, Dougherty G J, Blakey D C, Galbraith S M, Tozer G M, Holder A L, Naylor M A, Nolan J, Stratford M R, Chaplin D J, Hill S A. ZD6126: A Novel Vascular-targeting Agent that causes selective destruction of tumor vasculature. *Cancer Research*. 2002. 62(24): 7247–53.

10. Dorr, R. T.; Dvorakova, K.; Snead, K.; Alberts, D. S.; Salmon, S. E.; Pettit, G. R., Antitumor Activity of Combretastatin A4 Phosphate, a Natural Product Tubulin Inhibitor, *Invest. New Drugs*, 1996,14, 131.

11. Floyd. L. J.; Barnes, L. D.; Williams, R. F., Photoaffinity Labeling of Tubulin with (2-Nitro-4-azidophenyl) deacetylcolchicine: Direct Evidence for Two Colchicine Binding Sites, *Biochemistry*, 1989, 28, 8515.

12. Galbraith, Susan M.; Chaplin, David J.; Lee F, Stratford M R, Locke R J, Vojnovic B, Tozer G M. Effects of combretastatin A4 phosphate on endothelial cell morphology in vitro and relationship to tumour vascular targeting activity in vivo. *Anticancer Research*, 2001, 21:93–102.

13. Gerwick, W. H.; Proteau, P. J.; Nagle, D. G.; Hamel, E.; Blokhin, A.; Slate, D. L., Structure of Curacin A, a Novel Antimitotic, Antiproliferative, and Brine Shrimp Toxic Natural Product from the Marine Cyanobacterium *Lyngbya majuscula, J. Org. Chem.* 1994, 59, 1243.

14. Hahn, K. M.; Hastie, S. B.; Sundberg, R. J., Synthesis and Evaluation of 2-Diazo-3,3,3-trifluoropropanoyl Derivatives of Colchicine and Podophyllotoxin as Photoaffinity Labels: Reactivity, Photochemistry, and Tubulin Binding, *Photochem. Photobiol.* 1992, 55, 17.

15. Hamel, E., Antimitotic Natural Products and Their Interactions with Tubulin, *Medicinal Research Reviews*, 1996, 16, 207.

16. Hamel, E.; Lin, C. M., Separation of Active Tubulin and Microtubule-Associated Proteins by Ultracentrifugation and Isolation of a Component Causing the Formation of Microtubule Bundles, *Biochemistry*, 1984, 23, 4173–4184.

17. Hammonds, T. R.; Denyer, S. P.; Jackson, D. E.; Irving, W. L., Studies To Show That With Podophyllotoxin the Early Replicative Stages of Herpes Simplex Virus Type 1 Depend Upon Functional Cytoplasmic Microtubules, *J. Med. Microbiol.*, 1996, 45, 167.

18. Iyer S, Chaplin D J, Rosenthal D S, et al. Induction of apoptosis in proliferating human endothelial cells by the tumor-specific antiangiogenesis agent combretastatin A-4. *Cancer Res.* 1998; 58:4510–4514.

19. Jiang, J. B.; Hesson, D. P.; Dusak, B. A.; Dexter, D. L.; Kang, G. J.; Hamel, E., Synthesis and Biological Evaluation of 2-Styrylquinazolin-4(3H)-ones, a New Class of Antimitotic Anticancer Agents Which Inhibit Tubulin Polymerization, *J. Med. Chem.* 1990, 33, 1721.

20. Kanthou C, Tozer G M. The tumor vascular targeting agent CA4P induces reorganization of the actin cytoskeleton and early membrane blebbing in human endothelial cells. *Blood.* 2002. 99(6):2060–9.

21. Kingston, D. G. I.; Samaranayake, G.; Ivey, C. A., The Chemistry of Taxol, a Clinically Useful Anticancer Agent, *J. Nat. Prod.* 1990, 53, 1.

22. Kobayashi, S.; Nakada, M.; Ohno, M., Synthetic Study on an Antitumor Antibiotic Rhizoxin by Using an Enzymatic Process on Prochiral beta-Substituted Glutarates, *Pure Appl. chem.* 1992, 64, 1121.

23. Kobayashi, S.; Nakada, M.; Ohno, M., Synthetic Study on an Antitumor Antibiotic Rhizoxin by Using an Enzymatic Process on Prochiral beta-Substituted Glutarates *Indian J. Chem., Sect. B.* 1993, 32B, 159.

24. Lavielle, G.; Havtefaye, P.; Schaeffer, C.; Boutin, J. A.; Cudennec, C. A.; Pierre, A., New α-Amino Phosphonic Acid Derivatives of Vinblastine: Chemistry and Antitumor Activity, *J. Med. Chem.* 1991, 34, 1998.

25. Lejeune P, Hodge T G, Vrignaud, Bissery M -C. In vivo antitumor activity and tumor necrosis induced by AVE8062A, a tumor vasculature targeting agent. Proceedings of the AACR. ABSTRACT#781. 2002, 43: 156.

26. Lin, C. M.; Ho, H. H.; Pettit, G. R.; Hamel, E., Antimitotic Natural Products Combretastatin A-4 and Combretastatin A-2: Studies on the Mechanism of Their Inhibition of the Binding of Colchicine to Tubulin, *Biochemistry* 1989, 28, 6984.

27. Monks, A.; Scudiero, D.; Skehan, P.; Shoemaker, R.; Paull, K.; Vistica, D.; Hose, C.; Langley, J.; Cronise, P.; Vaigro-Wolff, A.; Gray-Goodrich; Campbell; Mayo; Boyd, M., Feasibility of a High-Flux Anticancer Drug Screen Using a Diverse Panel of Cultured Human Tumor Cell Lines, *J. Natl. Cancer Inst.*, 1991, 83, 757–766.

28. Mossman, T. Rapid calorimetric assay for cellular growth and survival: application to proliferation and cytotoxicity assay. *J. Immunol. Methods*, 1983, 16, 195–200.

29. Nakada, M.; Kobayashi, S.; Iwasaki, S.; Ohno, M., The First Total Synthesis of the Antitumor Macrolide Rhizoxin: Synthesis of the Key Building Blocks, *Tetrahedron Lett.* 1993, 34, 1035.

30. Nicolaou, K. C., Winssinger, N., Pastor, J., Ninkovic, S., Sarabia, F., He, Y., Vourloumis, D., Yang, Z., Oi, T., Giannakakou, P., Hamel, E., Synthesis of Epothilones A and B in Solid and Solution Phase, *Nature*, 1997, 387, 268–272.

31. Nogales, E., Wolf, S. G., and Downing, K. H., Structure of the α,β Tubulin Dimer by Electron Crystallography, *Nature*, 1998, 391, 199–203.

32. Owellen, R. J.; Hartke, C. A.; Kickerson, R. M.; Hains, F. O., Inhibition of Tubulin-Microtubule Polymerization by Drugs of the Vinca Alkaloid Class, *Cancer Res.* 1976, 36, 1499.

33. Pettit, G. R.; Rhodes, M. R., Antineoplastic agents 393. Synthesis of the trans-isomer of CA4P. *Anti-Cancer Drug Des.*, 1998, 13, 183.

34. Pettit, G. R., Srirangam, J. K., Barkoczy, J., Williams, M. D., Boyd, M. R., Hamel, E., Pettit, R. K., Hogan F., Bai, R., Chapuis, J. C., McAllister, S. C., Schmidt, J. M., Antineoplastic Agents 365: Dolastatin 10 SAR Probes, *Anti-Cancer Drug Des.*, 1998, 13, 243–277.

35. Pettit, G. R., Toki, B., Herald, D. L., Verdier-Pinard, P., Boyd, M. R., Hamel, E., Pettit, R. K., Antineoplastic Agents 379. Synthesis of Phenstatin Phosphate, *J. Med. Chem.*, 1998, 41, 1688–1695.

36. Pettit, G. R.; Cragg, G. M.; Singh, S. B., Antineoplastic agents, 122. Constituents of Combretum caffrum, *J. Nat. Prod.* 1987, 50, 386.

37. Pettit, G. R., Kamano, Y., Herald, C. L., Tuinman, A. A., Boettner, F. E., Kizu, H., Schmidt, J. M., Baczynskyj, L., Tomer, K. B., Bontems, R. J., The Isolation and Structure of a Remarkable Marine Animal Antineoplastic Constituent: Dolastatin 10, *J. Am. Chem. Soc.*, 1987, 109, 6883–6885.

38. Pettit, G. R.; Singh, S. B.; Cragg, G. M., Synthesis of Natural (−)-Combretastatin, *J. Org. Chem.* 1985, 50, 3404.

39. Pettit, G. R.; Cragg, G. M.; Herald, D. L.; Schmidt, J. M.; Lohavanijaya, P., Isolation and Structure of combretastatin, *Can, J. Chem.* 1982, 60, 1374.

40. Pinney K. G.; Bounds, A. D.; Dingeman K. M.; Mocharla, V. P.; Pettit, G. R.; Bai, R.; and Hamel E. A new Anti-tubulin agent containing the Benzo[b]thiophene Ring System. *Bioorg. Med. Chem. Lett.* 1999, 9, 1081–1086.

41. Rao, A. V. R.; Bhanu, M. N.; Sharma, G. V. M., Studies Directed Towards the Total Synthesis of Rhizoxin: Stereoselective Synthesis of C-12 to C-18 Segment, *Tetrahedron Lett.* 1993, 34, 707.

42. Rao, S.; Horwitz, S. B.; Ringel, I., Direct Photoaffinity Labeling of Tubulin with Taxol, *J. Natl. Cancer Inst.*, 1992, 84, 785.

43. Rao, A. V. R.; Sharma, G. V. M.; Bhanu, M. N., Radical Mediated Enantioselective Construction of C-1 to C-9 Segment of Rhizoxin, *Tetrahedron Lett.* 1992, 33, 3907.

44. Safa, A. R.; Hamel, E.; Felsted, R. L., Photoaffinity Labeling of Tubulin Subunits with a Photoactive Analog of Vinblastine, *Biochemistry* 1987, 26, 97.

45. Sawada, T.; Kato, Y.; Kobayashi, H.; Hashimoto, Y.; Watanabe, T.; Sugiyama, Y.; Iwasaki, S., A Fluorescent Probe and a Photoaffinity Labeling Reagent to Study the Binding Site of Maytansine and Rhizoxin on Tubulin, *Bioconjugate Chem.*, 1993, 4, 284. 31.

46. Sawada, T.; Kobayashi, H.; Hashimoto, Y.; Iwasaki, S., Identification of the Fragment Photoaffinity-labeled with Azidodansyl-rhizoxin as Met-363-Lys-379 on beta-Tubulin, *Biochem. Pharmacol.* 1993, 45, 1387.

47. Schiff, P. B.; Fant, J.; Horwitz, S. B., Promotion of Microtubule Assembly In Vitro by Taxol, *Nature*, 1979, 277, 665.

48. Staretz, M. E.; Hastie, S. B., Synthesis, Photochemical Reactions, and Tubulin Binding of Novel Photoaffinity Labeling Derivatives of Colchicine, *J. Org. Chem.* 1993, 58, 1589.

49. Swindell, C. S.; Krauss,N. E.; Horwitz, S. B.; Ringel, I., Biologically Active Taxol Analogs with Deleted A-ring Side Chain Substituents and Variable C-2' Configurations, *J. Med. Chem.* 1991, 34, 1176. (d) Pamess, J.; Horwitz, S. B., Taxol Binds to Polymerized Tubulin In Vitro, *J. Cell Biol.* 1981, 91, 479.

50. Tozer, G. M.; Prise, V. E.; Wilson, J.; Locke, R. J.; Vojnovic, B.; Stratford, M. R. L.; Dennis, M. F.; Chaplin, D. J., Combretastatin A-4 Phosphate as a Tumor Vascular-Targeting Agent: Early Effects in Tumors and Normal Tissues. *Cancer Res.*, 1999, 59, 1626.

51. Williams, R. F.; Mumford, C. L.; Williams, G. A.; Floyd, L. J.; Aivaliotis, M. J.; Martinez, R. A.; Robinson, A. K.; Barnes, L. D., A Photoaffinity Derivative of Colchicine: 6-(4'-Azido-2'-nitrophenylamino)hexanoyldeacetylcolchicine: Photolabeling and Location of the Colchicine-binding Site on the alpha-subunit of Tubulin, *J. Biol. Chem.* 1985, 260, 13794.

52. Zhang, X.; Smith, C. D., Microtubule Effects of Welwistatin, a Cyanobacterial Indolinone that Circumvents Multiple Drug Resistance, *Molecular Pharmacology*, 1996, 49, 288.

What is claimed is:

1. A compound of the following Formula I':

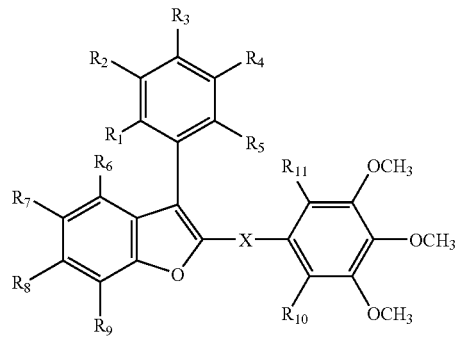

wherein:
$R_1$ through $R_{11}$ are independently selected from the group consisting of H, OH, Alkyl, Aryl, Benzyl, Amine, Halogen, Lower Alkoxy, Phosphate, Phosphoramidate, and Amino Acid Acyl, provided that at least one of $R_1$, $R_2$, $R_3$, $R_4$, or $R_5$ is lower alkoxy, and X is a single covalent bond, oxygen, or a carbonyl group.

2. The compound of the Formula I' as in claim 1, wherein:
at least one of $R_6$, $R_7$, $R_8$, or $R_9$ are lower alkoxy
and the remaining $R_1$, $R_2$, $R_3$, $R_4$ through $R_{11}$ are independently selected from the group consisting of H, OH, Halogen, Amine, Alkyl, Aryl, Benzyl, Lower Alkoxy, Phosphate, Phosphoramidate, or Amino Acid Acyl; and
X is single covalent bond, oxygen, or a carbonyl group.

3. The compound of claim 2, wherein:
$R_6$ or $R_8$ are lower alkoxy,
at least one of $R_1$, $R_2$, $R_3$, $R_4$, or $R_5$ is OH, amine, phosphate or phosphoramidate,
X is a single covalent bond,
and the remaining $R_1$ through $R_{11}$ are H.

4. The compound of claim 2 wherein:
$R_6$ or $R_8$ are lower alkoxy,
at least one of $R_1$, $R_2$, $R_3$, $R_4$, and $R_5$ is OH, amine, phosphate or phosphoramidate,
X is oxygen,
and the remaining $R_1$ through $R_{11}$ are H.

5. The compound of claim 2, wherein:
$R_6$ or $R_8$ are lower alkoxy,
at least one of $R_1$, $R_2$, $R_3$, $R_4$, and $R_5$ is OH, amine, phosphate or phosphoramidate,
X is a carbonyl,
and the remaining $R_1$ through $R_{11}$ are H.

6. A method for treating a vascular proliferative disorder in an animal comprising administering to an animal an effective amount of a compound of Formula I

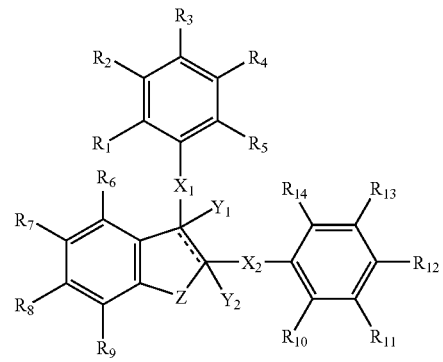

wherein:

R$_1$ through R$_{14}$ are independently selected from the group consisting of H, OH, Alkyl, Aryl, Benzyl, Amine, Halogen, Lower Alkoxy, Phosphate, Phosphoramidate, or Amino Acid Acyl, === is a single or double covalent bond, Y$_1$ and Y$_2$ are H or OH when === is a single covalent bond, X$_1$ and X$_2$ are a single covalent bond, oxygen, or a carbonyl group, and Z is O.

7. The method of claim 6 wherein the vascular proliferative disorder is characterized by the presence of malignant proliferating vasculature.

8. The method of claim 7 wherein the malignant proliferating vasculature is associated with a tumor or other neoplastic disease.

9. The method of claim 6 wherein the vascular proliferative disorder is characterized by the presence of nonmalignant proliferating vasculature.

10. The method of claim 9 wherein the nonmalignant proliferating vasculature is associated with an ocular disease selected from the group consisting of wet or age-related macular degeneration, diabetic retinopathy, retinopathy of prematurity, diabetic molecular edema, uveitis, or corneal neovascularization.

11. The method of claim 9 wherein the nonmalignant proliferating vasculature is associated with a nonocular disease state from selected from the group consisting of psoriasis, rheumatoid arthritis, atheroma, restenosis, Kaposi's sarcoma, haemangioma, or inflammatory disease.

12. A method for selectively reducing the flow of blood to at least a portion of a neoplastic region, comprising administering an effective amount of a compound the following Formula I:

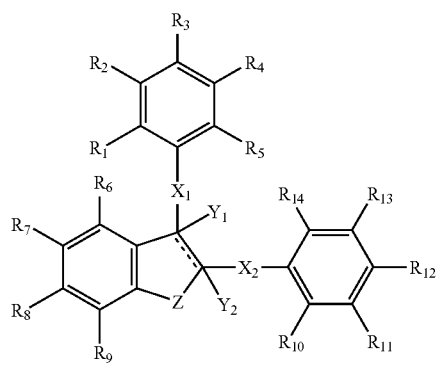

I wherein:

R$_1$ through R$_{14}$ are independently selected from the group consisting of H, OH, Alkyl, Aryl, Benzyl, Amine, Halogen, Lower Alkoxy, Phosphate, Phosphoramidate, or Amino Acid Acyl, === is a single or double covalent bond, Y$_1$ and Y$_2$ are H or OH when === is a single covalent bond, X$_1$ and X$_2$ are a single covalent bond, oxygen, or a carbonyl group, and Z is O, thereby causing substantial necrosis of tissue in the neoplastic region without substantial necrosis of tissue in adjoining regions.

13. The method of claim 12 wherein the reduction in tumor blood flow is reversible such that normal tumor blood flow is restored following cessation of treatment.

14. A method for treating neoplastic disease in an animal comprising administering to an animal an antiproliferative amount of a compound of Formula I:

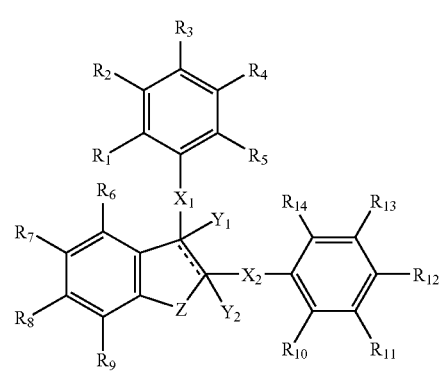

I wherein:

R$_1$ through R$_{14}$ are independently selected from the group consisting of H, OH, Alkyl, Aryl, Benzyl, Amine, Halogen, Lower Alkoxy, Phosphate, Phosphoramidate, or Amino Acid Acyl, === is a single or double covalent bond, Y$_1$ and Y$_2$ are H or OH when === is a single covalent bond, X$_1$ and X$_2$ are a single covalent bond, oxygen, or a carbonyl group, and Z is O.

15. The method of claim 14 wherein the compound has the direct result of causing tumor cell cytotoxicity due to inhibition of mitosis.

16. A method for inhibiting tubulin polymerization by contacting a tubulin-containing system with a compound of Formula I:

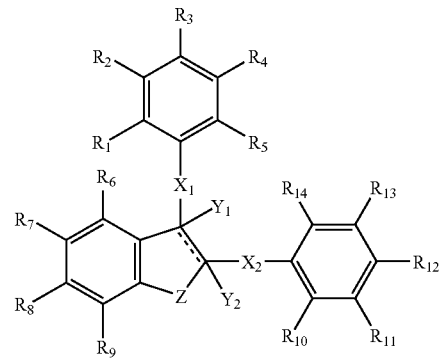

I wherein:
R$_1$ through R$_{14}$ are independently selected from the group consisting of H, OH, Alkyl, Aryl, Benzyl, Amine, Halogen, Lower Alkoxy, Phosphate, Phosphoramidate, or Amino Acid Acyl,
==== is a single or double covalent bond,
Y$_1$ and Y$_2$ are H or OH when ==== is a single covalent bond,
X$_1$ and X$_2$ are a single covalent bond, oxygen, or a carbonyl group, and
Z is O.

17. The method of claim 16 wherein said system is a tumor cell.

18. A pharmaceutical formulation containing a compound of Formula I:

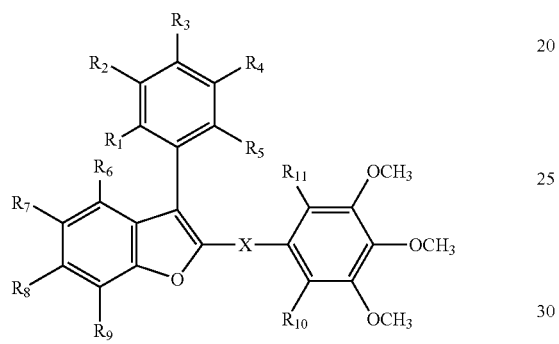

wherein:
R$_1$ through R$_{14}$ are independently selected from the group consisting of H, OH, Alkyl, Aryl, Benzyl, Amine, Halogen, Lower Alkoxy, Phosphate, Phosphoramidate, or Amino Acid Acyl, provided that at least one of R$_1$, R$_2$, R$_3$, R$_4$, or R$_5$ is lower alkoxy,
X is a single covalent bond, oxygen, or a carbonyl group, and a pharmaceutically suitable carrier.

19. The compound of claim 1, wherein R$_3$ is methoxy.
20. The compound of claim 1, wherein R$_8$ is methoxy.
21. A compound of the formula:

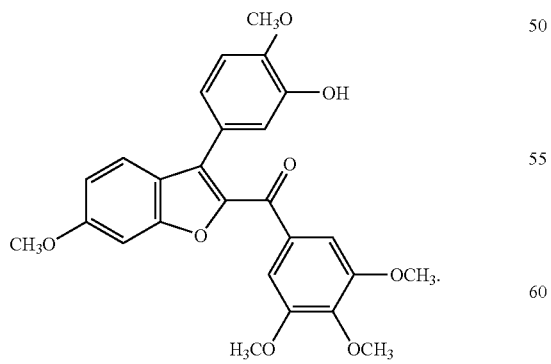

22. A compound of the formula:

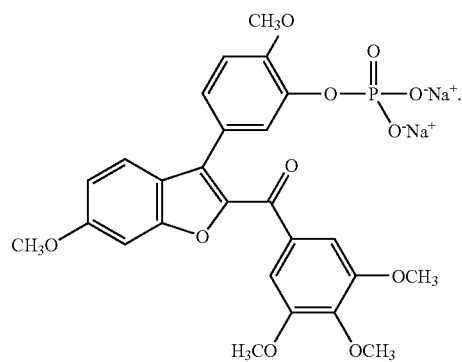

23. A compound of the formula:

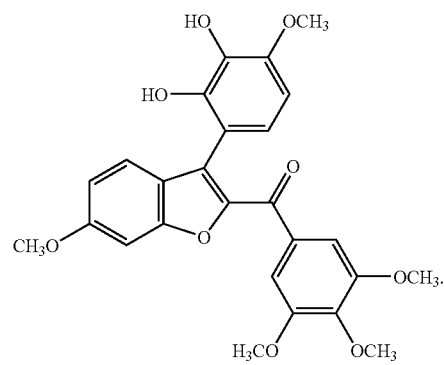

24. A compound of the formula:

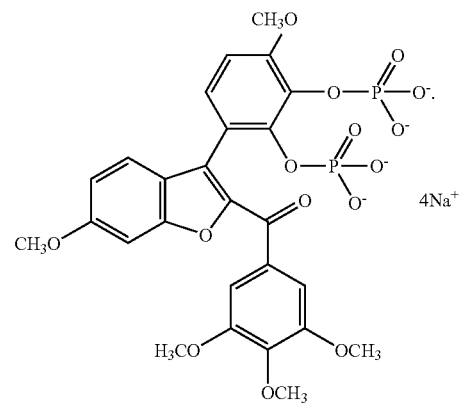

25. A method for treating a vascular proliferative disorder in an animal comprising administering to an animal an effective amount of a compound of Formula I':

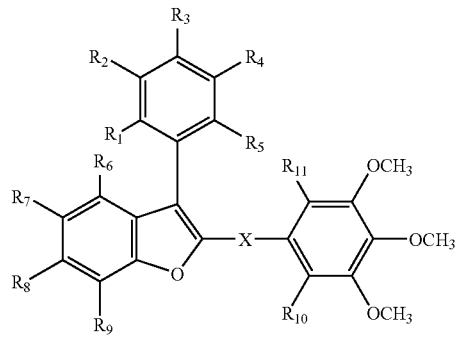

wherein:
R$_1$ through R$_{11}$ are independently selected from the group consisting of H, OH, Alkyl, Aryl, Benzyl, Amine, Halogen, Lower Alkoxy, Phosphate, Phosphoramidate, and Amino Acid Acyl, provided that at least one of R$_1$, R$_2$, R$_3$, R$_4$, or R$_5$ is lower alkoxy, and X is a single covalent bond, oxygen, or a carbonyl group.

26. A method for selectively reducing the flow of blood to at least a portion of a neoplastic region, comprising administering an effective amount of a compound the following Formula I':

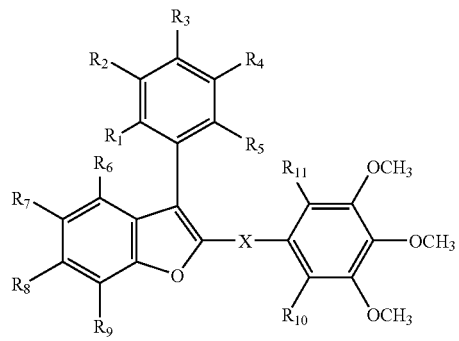

wherein:
R$_1$ through R$_{11}$, are independently selected from the group consisting of H, OH, Alkyl, Aryl, Benzyl, Amine, Halogen, Lower Alkoxy, Phosphate, Phosphoramidate, and Amino Acid Acyl, provided that at least one of R$_1$, R$_2$, R$_3$, R$_4$, or R$_5$ is lower alkoxy, and X is a single covalent bond, oxygen, or a carbonyl group.

27. A method for treating neoplastic disease in an animal comprising administering to an animal an antiproliferative amount of a compound of Formula I':

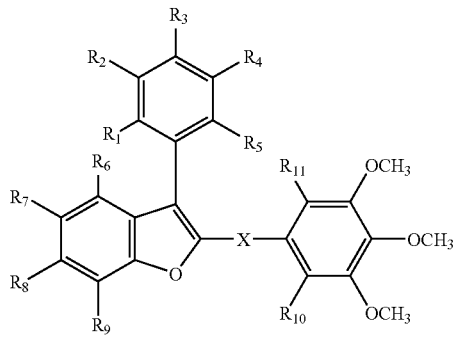

wherein:
R$_1$ through R$_{11}$ are independently selected from the group consisting of H, OH, Alkyl, Aryl, Benzyl, Amine, Halogen, Lower Alkoxy, Phosphate, Phosphoramidate, and Amino Acid Acyl, provided that at least one of R$_1$, R$_2$, R$_3$, R$_4$, or R$_5$ is lower alkoxy, and X is a single covalent bond, oxygen, or a carbonyl group.

28. A method for inhibiting tubulin polymerization by contacting a tubulin-containing system with a compound of Formula I':

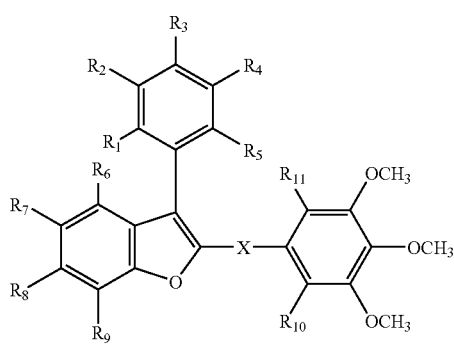

wherein:
R$_1$ through R$_{11}$ are independently selected from the group consisting of H, OH, Alkyl, Aryl, Benzyl, Amine, Halogen, Lower Alkoxy, Phosphate, Phosphoramidate, and Amino Acid Acyl, provided that at least one of R$_1$, R$_2$, R$_3$, R$_4$, or R$_5$ is lower alkoxy, and X is a single covalent bond, oxygen, or a carbonyl group.

* * * * *